US008741832B2

(12) United States Patent
Acharya et al.

(10) Patent No.: US 8,741,832 B2
(45) Date of Patent: Jun. 3, 2014

(54) PEGYLATED ALBUMIN AND USES THEREOF

(75) Inventors: Seetharama A. Acharya, Cresskill, NJ (US); Belur N. Manjula, Cresskill, NJ (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 1377 days.

(21) Appl. No.: 11/921,064

(22) PCT Filed: Jun. 9, 2006

(86) PCT No.: PCT/US2006/022463
§ 371 (c)(1),
(2), (4) Date: Jun. 12, 2009

(87) PCT Pub. No.: WO2006/135740
PCT Pub. Date: Dec. 21, 2006

(65) Prior Publication Data
US 2009/0298746 A1 Dec. 3, 2009

Related U.S. Application Data

(60) Provisional application No. 60/689,175, filed on Jun. 10, 2005.

(51) Int. Cl.
A61K 38/00 (2006.01)
C07K 1/00 (2006.01)
C07K 14/00 (2006.01)
C07K 16/00 (2006.01)
C07K 17/00 (2006.01)
C07K 14/76 (2006.01)
C07K 14/805 (2006.01)

(52) U.S. Cl.
CPC .............. *A61K 38/00* (2013.01); *C07K 14/76* (2013.01); *C07K 14/805* (2013.01)
USPC .......................................... 514/1.1; 530/362

(58) Field of Classification Search
None
See application file for complete search history.

(56) References Cited

U.S. PATENT DOCUMENTS

| 4,970,298 | A | * | 11/1990 | Silver et al. .................. 530/356 |
| 5,585,484 | A | | 12/1996 | Acharya et al. |
| 5,585,489 | A | * | 12/1996 | Russ et al. .................... 544/76 |
| 5,741,893 | A | * | 4/1998 | Hsia ............................ 530/385 |
| 5,750,725 | A | | 5/1998 | Acharya et al. |
| 6,017,943 | A | | 1/2000 | Acharya et al. |
| 6,310,039 | B1 | * | 10/2001 | Kratz ........................... 514/19.5 |
| 6,371,975 | B2 | | 4/2002 | Cruise et al. |
| 6,458,147 | B1 | | 10/2002 | Cruise et al. |
| 6,670,323 | B1 | | 12/2003 | Lee et al. |
| 6,773,613 | B1 | | 8/2004 | Winslow et al. |
| 6,844,317 | B2 | | 1/2005 | Winslow et al. |
| 6,875,423 | B1 | | 4/2005 | Intaglietta et al. |
| 6,887,952 | B1 | * | 5/2005 | Buechler et al. ............... 525/532 |
| 7,019,117 | B2 | | 3/2006 | Acharya et al. |
| 7,037,895 | B2 | * | 5/2006 | Assaly et al. .................. 514/13.5 |
| 7,038,016 | B2 | | 5/2006 | Talarico et al. |
| 7,144,989 | B2 | | 12/2006 | Acharya et al. |
| 7,169,900 | B2 | | 1/2007 | Acharya et al. |
| 7,271,145 | B2 | | 9/2007 | Winslow et al. |
| 7,501,499 | B2 | | 3/2009 | Acharya et al. |
| 7,521,174 | B2 | | 4/2009 | Acharya et al. |
| 8,071,546 | B2 | * | 12/2011 | Cabrales et al. ............... 514/15.2 |
| 2003/0004105 | A1 | * | 1/2003 | Assaly et al. .................... 514/12 |
| 2003/0009145 | A1 | | 1/2003 | Struijker-Boudier et al. |
| 2003/0161809 | A1 | | 8/2003 | Houston et al. |
| 2004/0002443 | A1 | | 1/2004 | Acharya et al. |
| 2005/0026816 | A1 | | 2/2005 | Winslow et al. |
| 2005/0037966 | A1 | | 2/2005 | Ruben et al. |
| 2005/0159339 | A1 | | 7/2005 | Acharya et al. |
| 2005/0201988 | A1 | | 9/2005 | Acharya et al. |
| 2006/0111275 | A1 | | 5/2006 | Acharya et al. |
| 2009/0215670 | A1 | | 8/2009 | Acharya et al. |
| 2010/0216695 | A1 | | 8/2010 | Acharya et al. |
| 2010/0222260 | A1 | | 9/2010 | Cabrales et al. |

FOREIGN PATENT DOCUMENTS

| JP | 11-271306 | * | 8/1999 | ........... G01N 33/532 |
| WO | WO2005/097203 | * | 10/2005 | ............. A61K 47/48 |
| WO | WO 2007/050121 A2 | | 5/2007 | |
| WO | WO 2007/058678 A2 | | 5/2007 | |

OTHER PUBLICATIONS

Winslow et al. Comparison of PEG-modified albumin and hemoglobin in extreme hemodilution in the rat. J Appl Physiol. Published online Jun. 18, 2004. vol. 97, pp. 1527-1534.*
Pendri et al. Poly(ethylene glycol) Fluorescent Linkers. Bioconjugate Chem. 1995, vol. 6, pp. 596-598.*
Manjula et al. Site-Specific PEGylation of Hemoglobin at Cys-93(beta): Correlation between the Colligative Properties of the PEGylated Protein and the Length of the Conjugated PEG Chain. Bioconjugate Chem. 2003, vol. 14, pp. 464-472.*
Vandergriff et al. MP4, a new nonvasoactive PEG-Hb conjugate. Blood Components. Transfusion. Apr. 2003. vol. 43, pp. 509-516.*
Fujiwara et al. Novel enzyme immunoassay for thyrotropin-releasing hormone using N-(4-diazophenyl)maleimide as a coupling agent. FEBS. 1986, vol. 202, No. 2, pp. 197-201.*

(Continued)

*Primary Examiner* — Marcela M Cordero Garcia
(74) *Attorney, Agent, or Firm* — Amster, Rothstein & Ebenstein LLP

(57) ABSTRACT

The present invention provides PEGylated hemoglobins and PEGylated albumins comprising polyethylene glycol (PEG) conjugated to hemoglobin or to albumin, wherein the PEG is a maleimide PEG, an alkylamide PEG, an iodoacetamide PEG, a p-nitro thio-phenyl PEG, a vinyl sulfone PEG, or a mixed disulfide PEG; and PEGylated albumins and PEGylated hemoglobins comprising polyethylene glycol (PEG) attached to a thiolated amino group of albumin or hemoglobin, wherein the amino group is thiolated using dithio sulfo succinimidyl propionate (DTSSP) or dithiosuccinimidyl propionate (DTSP) or dithiobispropionimidate. The invention also provides methods of preparing PEGylated hemoglobins and PEGylated albumins comprising a) reacting hemoglobin or albumin with a thiolating agent and with a PEGylating agent, and b) capping unPEGylated reactive thiols of hemoglobin or albumin with N-ethyl maleimide.

7 Claims, 11 Drawing Sheets

(56) References Cited

OTHER PUBLICATIONS

Nacharaju et al. Surface decoration of red blood cells with maleimidophenyl-polyethylene glycol faciliatated by thiolation with iminothiolane: an apporach to mask A, B, and D antigens to generate universal red blood cells. Immunohematology. Transfusion. Mar. 2005, vol. 45, pp. 374-383.*

JP 11-271306. Fujita et al. Oct. 1999, Abstract English translation, 2 pages.*

Fleiner et al. Studies on Protein-Liposome Coupling Using Novel Thiol-Reactive Coupling Lipids: Influence of Spacer Length and Polarity. Bioconjugate Chemistry, 2001. vol. 12, pp. 470-475.*

Manjula et al. Cys-93-BBSuccinidophenyl Polyethylene Glycol 2000 Hemoglobin A. The Jornal of Biological Chemistry, 2000. vol. 275, Nol. 8, pp. 5527-5534.*

Swain et al. Unexpected Products from the Reaction of the Synthetic Cross-Linker 3,3'-Dithibis(Sulfosuccinimidyl Propionate), DTSSP with Peptides. Published online Mar. 17, 2004, vol. 15, pp. 736-749.*

Cabrales et al. Microvascular PO2 during extreme hemodilution with hemoglobin site specifically PEGylated at Cys-93(B) in hamster window chamber. Am J Physiol Heart Circ Physiol. First published Jun. 10, 2004, vol. 287, pp. H1609-H1617.*

Veronese et al. Peptide and protein PEGylation: a review of problems and solutions. Biomaterials, 2001, vol. 22, pp. 405-417.*

Manjula et al. Conjugation of Multiple Copies of Polyethylene Glycol to Hemoglobin Facilitated Through Thiolation: Influence on Hemoglobin Structure and Function. The Protein Journal, vol. 24, Nol. 3, Apr. 2005.*

PCT International Search Report received from the International Searching Authority dated Jan. 18, 2008 in connection with PCT International Patent Application No. PCT/US2006/22619, 5 pages.

PCT Written Opinion received from the International Searching Authority dated Jan. 18, 2008 in connection with PCT International Patent Application No. PCT/US2006/22619, 6 pages.

Wettstein R et al., entitled "Resuscitation From Hemorrhagic Shock With MalPEG-Albumin: Comparison With MalPEG-Hemoglobin," Shock, vol. 22, No. 4, pp. 351-357, 2004, pp. 351-356.

International Searching Authority, "International Search Report of the International Searching Authority," for International Application No. PCT/US2006/22463, 6 pages, Nov. 3, 2006.

International Searching Authority, "Written Opinion of the International Searching Authority," for International Application No. PCT/US2006/22463, 3 pages, Nov. 3, 2006.

* cited by examiner

PEGYLATED ALBUMIN AND USES THEREOF

CROSS-REFERENCE TO RELATED APPLICATIONS

This application is a national stage entry under 35 U.S.C. §371 of PCT International Patent Application No. PCT/US2006/022463, filed on Jun. 9, 2006, which claims priority to U.S. Provisional Patent Application No. 60/689,175, filed on Jun. 10, 2005, the contents of which are hereby incorporated by reference.

STATEMENT OF GOVERNMENT SUPPORT

This invention was made with government support under grant numbers HL58247 and HL71064 awarded by the National Institutes of Health (NIH), and grant number PR023085 awarded by the U.S. Army. Accordingly, the government has certain rights in the invention.

BACKGROUND OF THE INVENTION

Throughout this application various publications are referred to in parenthesis. Full citations for these references may be found at the end of the specification immediately preceding the claims. The disclosures of these publications are hereby incorporated by reference in their entireties into the subject application to more fully describe the art to which the subject application pertains.

Conjugation of polymers to peptide and protein therapeutics to generate hybrid molecules with unique and distinct molecular properties has become a popular approach to alter and/or control their stability, biodistribution, pharmacokinetics and toxicology. Since the pioneering work of Abuchowski et al. (1997a & b) of grafting polyethylene glycol (PEG) chains to albumin, PEGylation has been a very widely used conjugation approach to generate protein-polymer bio-conjugates of unique biological properties or diminished toxicities.

The first step of the PEGylation of proteins and peptides can involve functionalizing PEG with group specific reagents, so that the conjugation of PEG to protein can be targeted to specific side chain groups of the proteins, such as amino, carboxyl, sulfhydryl or guanidino groups. More recently, the strengths of site directed mutagenesis have also been integrated to achieve site specific PEGylation. Cysteine (Cys) residues can be introduced in a site specific fashion in place of preselected surface amino acid residues of proteins. The thiol groups of the newly introduced Cys residues can be targeted for PEGylation using maleimide chemistry based PEG reagents. Replacement of Serine (Ser) or Threonine (Thr) with Cys has an advantage that the net charge of the mutant protein is not altered as a result of the PEGylation, i.e. a conservative PEGylation protocol as far as the site directed mutagenesis of the parent protein is conservative.

A chemical approach to introduce new thiols on the ε-amino groups of proteins as a means of increasing accessibility of the surface amino groups for PEGylation and targeting the PEG reagents to these sites by maleimide chemistry has been developed (Acharya et al., 1996). The initial approach involved thiolation of amino groups of proteins using 2-iminothiolane. In a preferred protocol, protein is incubated with iminothiolane in the presence of PEG maleimide, and the new thiol groups generated in situ on the protein amino groups are trapped immediately by PEG maleimide as succinimidyl derivatives (Acharya et al., 2003).

Hemoglobin (Hb) based blood substitutes are being developed to overcome shortages of blood supply (Chang, 1999; Klein, 2000). The most extensively studied and financed blood substitute has been diaspirin cross-linked Hb. Though intramolecular crosslinking of Hb helped to overcome nephrotoxicity and high oxygen affinity of acellular Hb, the two major limitations of stroma-free Hb as a blood substitute (Chang, 1999), the product remained vasoactive (Alayash et al., 2001; Kramer, 2003; Winslow, 2000). The vasoactivity has been attributed to the extravasation of acellular Hb and the scavenging of nitric oxide (NO) by the extravasated Hb.

Enhancing the molecular size of Hb by oligomerization to prevent or reduce the extravasation of Hb has been one of the solutions advanced to overcome the vasoactivity of acellular Hb, while another is to lower the affinity of Hb to nitric oxide by site directed mutagenesis. Animal studies have shown that both approaches reduce the pressor effect of Hb (Gulati et al., 1999).

An alternate approach to overcome the vasoactivity of Hb involves engineering the properties of plasma volume expanders into Hb, namely high viscosity and high colloidal osmotic pressure to Hb (Acharya et al., 2005). Enzon PEGylated bovine Hb, which carries ten copies of PEG-5K chains, was found to be nonhypertensive even though its affinity for NO is comparable to that of other modified Hbs that are under clinical trial. The unusual molecular properties of Enzon PEGylated bovine Hb, namely enhanced molecular volume, high viscosity and high colloidal osmotic pressure, which are also the properties of plasma volume expanders, have been attributed as the molecular basis of the neutralization of vasoactivity of acellular Hb. Accordingly, PEGylation of Hb has been considered as an approach to generate non-hypertensive Hb. This application of polyethylene glycol (PEG), a water-soluble, inert and nontoxic polymer, reflects a very different translation of PEGylation than other applications of other molecular properties induced to proteins by PEGylation, where PEGylation-induced increased solubility, increased half-life, and reduced access of molecular surface to the immune system are used to generate PEG-protein conjugates of therapeutic value (Bailon and Berthold, 1998; Harris et al., 1997, 2003).

In an attempt to establish that the neutralization of vasoactivity is a generalized consequence of PEGylation induced molecular properties of acellular Hb and not unique to Enzon PEGylated bovine Hb, a hexaPEGylated human Hb [(SP-PEG-5K)$_6$-Hb] was generated using a PEGylation platform referred to as extension arm facilitated PEGylation protocol (Acharya et al., 2005; Manjula et al., 2005). This hexaPEGylated Hb exhibited an unusually high increase in the molecular volume, increased viscosity and higher colloidal osmotic pressure and was non-hypertensive.

The non-hypertensive PEGylated human Hb, (SP-PEG5K)$_6$-Hb, carries only six copies of PEG-5K chains while the Enzon PEGylated bovine Hb carries ten copies of PEG-5K chains. In addition, the chemistry of conjugation of PEG-chains in the two products is very distinct. In the decaPEGylated bovine Hb of Enzon, the PEG-chains are conjugated to the surface amino groups of Hb through an urethane linkage, which results in the loss of the positive charge of the ε-amino group of Lysine (Lys) residues to which PEG chains are conjugated. In the hexaPEGylated human Hb, the PEG-5K chains are conjugated to the surface amino groups using the extension arm facilitated PEGylation. In this protocol, the surface amino groups are first reacted with iminothiolane, which results in the extension of the side chain of Lys residues by the linking of δ-mercapto butirimidyl chains, and the thiol groups of the extension arm are modified with maleimide PEG (Acharya et al., 2005; Manjula et al. 2005). The higher efficiency of the PEG-chains of hexaPEGylated Hb to neutralize the vasoactivity could be a correlate of the fact that the extension arm facilitated PEGylation conjugates the PEG-chains without changing the surface charge of Hb, i.e. the PEGylation is conservative. Since the colloidal osmotic pressure (COP) of the hexaPEGylated Hb is comparable to that of decaPEGylated Hb, the results reflect the role of the conservation of the positive charge of Hb at the sites of PEGylation. When the surface charge is conserved, the PEG-chains conjugated are possibly more efficient in inducing the desirable molecular properties to Hb that facilitates the neutralization of its vasoactivity.

To gain further insight into the possible advantages of conserving the surface charges at the site of the conjugation, another hexaPEGylated Hb has been generated in which the charge of the surface amino groups is conserved. ω-methoxy PEG 5K-propoinaldehyde is conjugated to Hb in the presence of sodium cyanoborohydride (reductive alkylation chemistry). The molecular properties of this PEG-Hb conjugate, particularly the COP of (Propyl-PEG5K)$_6$-Hb was considerably higher than that of [(SP-PEG-5K)$_6$-Hb], leading to the suggestion that either the chemistry of conjugation of PEG-chains to Hb or the site selectivity of PEGylation of Hb influences the molecular properties of the PEG-Hb (Hu et al., 2005).

SUMMARY OF THE INVENTION

The present invention provides PEGylated hemoglobins and PEGylated albumins comprising a polyethylene glycol (PEG) conjugated to hemoglobin or to albumin, wherein the PEG is a maleimide PEG, an alkylamide PEG, an iodoacetamide PEG, a p-nitro thio-phenyl PEG, a vinyl sulfone PEG, or a mixed disulfide PEG.

The invention also provides a PEGylated albumin or a PEGylated hemoglobin comprising a polyethylene glycol (PEG) attached to a thiolated amino group of albumin or hemoglobin, wherein the amino group is thiolated using dithio sulfo succinimidyl propionate (DTSSP) or dithiosuccinimidyl propionate (DTSP) or dithiobispropionimidate.

The invention provides a method of preparing a PEGylated hemoglobin or a PEGylated albumin comprising: a) reacting hemoglobin or albumin with a thiolating agent to produce thiolated hemoglobin or thiolated albumin; b) reacting the thiolated hemoglobin or the thiolated albumin with a PEGylating agent; and c) capping unPEGylated reactive thiols of hemoglobin or albumin with a capping agent.

The invention further provides a method of preparing a PEGylated hemoglobin or a PEGylated albumin comprising: a) reacting hemoglobin or albumin with dithio sulfo succinimidyl propionate (DTSSP) or with dithiosuccinimidyl propionate (DTSP) or with dithiobispropionimidate to thiolate the hemoglobin or albumin, and b) reacting the thiolated hemoglobin or the thiolated albumin with a PEGylating agent.

The invention still further provides compositions and blood substitutes (plasma volume expanders) comprising PEGylated hemoglobins and PEGylated albumins and methods of treating a subject which comprise administering to the subject any of the PEGylated hemoglobins or PEGylated albumins disclosed herein.

Additional objects of the invention will be apparent from the description which follows.

DETAILED DESCRIPTION OF THE INVENTION

Figure 1:
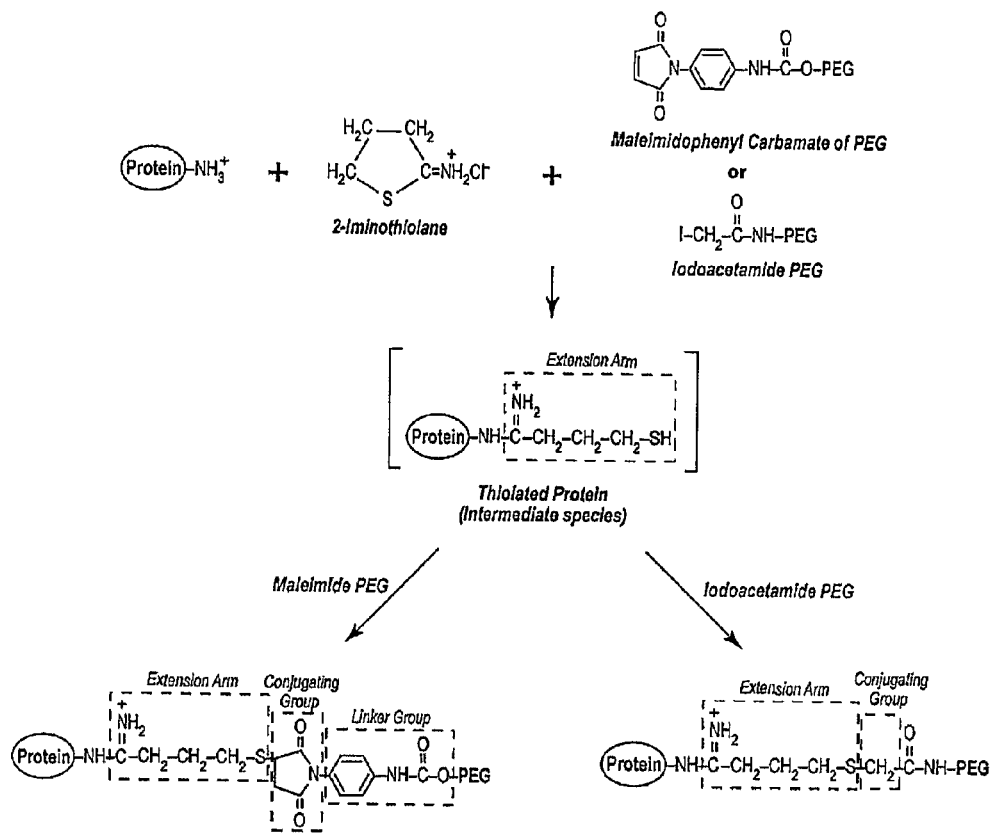
FIG. 1. Schematic representation of thiolation mediated conservative PEGylation of proteins. The thiol groups of the thiolated protein generated as an intermediate in this protocol can be the target sites for PEG reagents with sulfhydryl group specific functional groups. PEGylation of the protein based on the reaction of monofunctional PEG maleimide and monofunctional iodoacetamido PEG have been used as specific examples to demonstrate the conservative PEGylation reaction.

The present invention is directed to a PEGylated hemoglobin or a PEGylated albumin comprising a polyethylene glycol (PEG) conjugated to hemoglobin or to albumin, wherein the PEG is a maleimide PEG, an alkylamide PEG, an iodoacetamide PEG, a p-nitro thio-phenyl PEG, a vinyl sulfone PEG, or a mixed disulfide PEG.

As used herein, "PEGylation" means linking to polyethylene glycol (PEG), and a "PEGylated" hemoglobin or albumin is a hemoglobin or albumin that has PEG conjugated to it.

In a preferred embodiment, the PEGylated hemoglobin is a carboxamidomethyl (CAM) PEGylated hemoglobin.

The maleimide PEG can be, for example, a maleimide PEG comprising an alkyl linker or, preferably, a maleimide phenyl PEG. The PEG can be attached to albumin or hemoglobin via a linker and/or an extension arm. As used herein, an "extension arm" refers to the carbon chain-thiol group that is attached to albumin or hemoglobin during a thiolation process. The extension arm places the thiol group away from the surface of the albumin or hemoglobin, thereby enhancing the accessibility of the thiol group to bulky PEG reagents. The linker may comprise an alkyl, aryl and/or heteroaryl group. For example, the alkyl group can be a propyl group, and the aryl group can be a phenyl group. The linker or extension arm may comprise a δ-mercapto butyrimidyl chain or a γ-mercapto propylamide chain.

The invention also provides a PEGylated albumin or a PEGylated hemoglobin comprising a polyethylene glycol (PEG) attached to a thiolated amino group of albumin or hemoglobin, wherein the amino group is thiolated using dithio sulfo succinimidyl propionate (DTSSP) or dithiosuccinimidyl propionate (DTSP) or dithiobispropionimidate.

The invention further provides thiocarbamoyl PEGylated albumin, PEGylated thiolated albumin, PEGylated polynitroxylated albumin, and methods of preparing these PEGylated albumins.

Each PEG chain may have a molecular weight of 200 daltons to 20,000 daltons, preferably 3,000 to 5,000 daltons, and more preferably 5,000 daltons. PEGs of various molecular weights, conjugated to various groups, can be obtained commercially, for example from Nektar Therapeutics, Huntsville, Ala.

In one embodiment, the PEGylated albumin has a molecular weight of about 130 kDa. In one embodiment, the PEGylated albumin has a molecular radius of 8-9 nm. There may be between 6-18 PEG chains conjugated to albumin. In one preferred embodiment, 12 PEG chains are conjugated to albumin. Preferably, the PEGylated albumin has a colloid osmotic pressure of 37-40 mm Hg. Preferably, the PEGylated albumin has a viscosity of 2.0 to 4.0 cP.

In one embodiment, the PEGylated hemoglobin has a molecular radius of 5-6 nm. There may be between 2-8 PEG chains conjugated to hemoglobin. In a preferred embodiment, 4-6 PEG chains are conjugated to hemoglobin. Preferably, the PEGylated hemoglobin has a colloid osmotic pressure of 34-36 mm Hg. The PEGylated hemoglobin can have a viscosity of 2.0 to 4.0 cP.

Preferably, the hemoglobin that is PEGylated contains an intramolecular crosslink. Examples of intramolecular crosslinks include αα-crosslinking and ββ-crosslinking. Preferably, crosslinking the hemoglobin increases the molecular volume of the PEGylated crosslinked hemoglobin. Preferably, crosslinking the hemoglobin decreases the colloidal osmotic pressure of the PEGylated crosslinked hemoglobin.

The PEGylation procedure can be selected so that PEGylation does not alter the surface charge of albumin or hemoglobin or so that PEGylation does alter the surface charge of albumin or hemoglobin.

Preferably, PEGylation does not impair drug binding ability of albumin.

The invention provides a method of preparing a PEGylated hemoglobin or a PEGylated albumin comprising:
  a) reacting hemoglobin or albumin with a thiolating agent to produce thiolated hemoglobin or thiolated albumin;
  b) reacting the thiolated hemoglobin or the thiolated albumin with a PEGylating agent; and
  c) capping unPEGylated reactive thiols of hemoglobin or albumin with a capping agent, such as, for example, N-ethyl maleimide.

The thiolating agent can be, for example, iminothiolane, dithio sulfo succinimidyl propionate (DTSSP) or dithiosuccinimidyl propionate (DTSP) or dithiobispropionimidate. The PEGylating agent can be, for example, an iodoacetamide PEG or a maleimide PEG.

The invention further provides a method of preparing a PEGylated hemoglobin or a PEGylated albumin comprising:
  a) reacting hemoglobin or albumin with dithio sulfo succinimidyl propionate (DTSSP) or with dithiosuccinimidyl propionate (DTSP) or with dithiobispropionimidate to thiolate the hemoglobin or albumin, and
  b) reacting the thiolated hemoglobin or the thiolated albumin with a PEGylating agent.

The PEGylating agent can be, for example, an iodoacetamide PEG or a maleimide PEG.

The methods can further comprise preparing a hemoglobin having an intramolecular crosslink. Examples of intramolecular crosslinking include αα-crosslinking and ββ-crosslinking.

The invention still further provides a PEGylated hemoglobin or a PEGylated albumin prepared by any of the methods disclosed herein.

The invention provides for the use of any mammalian albumin or hemoglobin, such as, for example, human hemoglobin, human serum albumin, and bovine serum albumin.

The invention also provides a composition comprising any of the PEGylated hemoglobins or PEGylated albumins disclosed herein or prepared by any of the methods disclosed herein, and a pharmaceutically acceptable carrier. The invention further provides a blood substitute (plasma volume expander) comprising any of the PEGylated hemoglobins or albumins disclosed herein or prepared by any of the methods disclosed herein. Pharmaceutically acceptable carriers include, but are not limited to, saline, phosphate buffered saline, Ringer's solution, lactated Ringer's solution, Locke-Ringer's solution, Kreb's Ringer's solution, Hartmann's balanced saline solution, and/or heparinized sodium citrate acid dextrose solution. The pharmaceutical compositions of the present invention may be administered by conventional means including but not limited to transfusion and injection. The invention provides methods of treating a subject which comprises administering to the subject any of the PEGylated hemoglobins or PEGylated albumins disclosed herein.

The present invention is illustrated in the following Experimental Details section, which is set forth to aid in the understanding of the invention, and should not be construed to limit in any way the scope of the invention as defined in the claims that follow thereafter.

EXPERIMENTAL DETAILS

I. Introduction

The PEGylation protocol, thiolation mediated maleimide chemistry (succinimidylation) based PEGylation, is schematically represented in FIG. 1. Reaction of the surface amino groups of the protein with 2-iminothiolane results in the δ-mercapto butyrimidination of the reactive surface ε-amino groups of its Lys residues, thereby introducing a four carbon atom extension arm between the ε-amino groups and the newly introduced thiol groups. The PEG maleimide then reacts with the thiol groups to conjugate the PEG-chains to the protein. Since the thiolating reagent, 2-iminothiolane, does not carry free thiol group and thiol groups are generated in situ on reaction of iminothiolane with the amino groups, the thiolating reagent and the PEG maleimide can be incubated together with the protein without any concern for the consumption of the maleimide PEG by the thiolating reagent. This approach is referred to as one step thiolation mediated maleimide chemistry based PEGylation of proteins. This approach is a preferred one over the two step thiolation mediated maleimide chemistry based PEGylation protocol, wherein thiolation is done in the absence of maleimide PEG and the PEGylation is carried out after the thiolation. Introduction of an 'extension arm' is a feature of this thiolation mediated PEGylation protocol. The strategy of introducing an extension arm on the ε-amino groups of Lys residues of protein provides an increased accessibility to the new thiol groups (as compared to the original amino groups) of the macromolecular PEG-reagent.

II. Maleimide PEG and Iodoacetamide PEG Based PEGylation of Hemoglobin

A modified protocol for PEGylation of Hb has been developed that generates a product with four to six PEG-5K chains (average number) per tetramer. One step protocol for PEGylation of proteins has been the preferred choice to overcome (or at least minimize) the increased potential of the thiolated Hb to participate in intermolecular cross linking of the protein at the higher protein concentration that is used in the new reaction conditions. In the new protocol, the PEGylation of Hb is carried out at a Hb concentration of 1 mM in the presence of 10 mM iminothiolane and 10 mM Maleimide phenyl PEG for 6 hours at 4° C. to generate Hb-PEG conjugate. This Hb-PEG conjugate exhibits a molecular size enhancement that is slightly higher than that of tetraPEGylated dog Hb, but smaller than that of the hexaPEGylated Hb [(SP-PEG-5K)$_6$-Hb] generated by PEGylation of Hb at a concentration of 0.5 mM in the presence of 5 mM iminothiolane and 10 mM maleimide phenyl PEG. The molecular radius of the new product and the results of the globin chain analysis clearly reflect that the new material carries less number of PEG-5K chains per tetramer than the previously characterized product, [(SP-PEG5K)$_6$-Hb].

In the design and generation of the non-hypertensive, hexaPEGylated Hb, it has been assumed that all the thiol groups generated in situ on Hb on its reaction with iminothiolane are completely trapped by maleimide PEG as succinimidyl phenyl PEG-derivatives. But given the multiplicity of the sites of thiolation exposed by the tryptic peptide mapping of the PEGylated protein, it is conceivable that the Hb-PEG conjugate may carry underivatized thiol groups. Recent studies indicated that some amount of higher molecular weight products are generated after storage at −80° C. over months. Since molecular size homogeneity is not a direct correlate of the site selectivity of thiolation, and appears to be a consequence of a degree of resistance of PEGylated Hb with six copies of PEG-5K chains to undergo further PEGylation, it is possible that at the end of the PEGylation reaction, the PEGylated Hb may still carry some unmodified thiols and these may be responsible for the molecular size heterogeneity generated during storage.

Accordingly, in developing this new protocol for generating Hb-PEG-5K conjugate that carries only four to six PEG-5K chains by the thiolation mediated maleimide chemistry based PEGylation, another modification of the procedure has also been introduced. A step of capping the un-derivatized thiol functions of the Hb-PEG conjugate using N-ethylmaleimide (NEM) has been introduced. This involves treatment of the reaction mixture containing PEGylated product generated after six hours of incubation with 10 mM N-ethylmaleimide. This step is expected to cap (derivatize) the thiols that are not modified by maleimide PEG. This product is then subjected to a tangential flow filtration step using Minim to isolate the PEGylated Hb free of PEG.

The physical properties of this new Hb-PEG adduct (SP-PEG5K-Hb) is compared with that of (SP-PEG5K)$_6$-Hb in Table 1. Based on the RP-HPLC analysis of the PEGylated Hb, and molecular mass analysis of the PEGylated chains, it has been calculated that new Hb-PEG adduct carries close to five PEG-chains (an average number). Since the Hb-PEG adduct is generated using a Hb concentration of 1 mM (64 mg/ml), this protocol reduces the amount of PEG reagent that needs to be used by half, as compared to that needed for the production of the hexaPEGylated Hb. Thus, this modified protocol will reduce the cost of production of Hb-PEG conjugate, the oxygen carrying plasma volume expanders.

PEGylation of hemoglobin (Hb) by the thiolation mediated iodoacetamide chemistry based PEGylation protocol has been carried out at a protein concentration of 1 mM, in the presence of 10 mM iminothiolane, and 10 mM iodoacetamide PEG-5000 at 4° C. for 6 hours. The unPEGylated reactive thiols of the protein are capped with N-ethyl maleimide by reacting with the reagent for another one hour. The product is then purified on a preparative Superose-12 column chromatography. The properties of this new PEG-Hb conjugate, carboxamidomethyl PEG-Hb [CAM-PEG5K-Hb], have been compared with that of [SP-PEG5K-Hb] prepared under the same conditions, in terms of molecular radius, hydrodynamic volume, colloidal osmotic pressure (4 g %) and RP-HPLC. (Table 1). As can be seen, retention times of these two products, the Hb-PEG-5K adducts generated by using maleimide-phenyl-PEG-5K and iodoacetamide PEG-5K are comparable, and slightly lower than that of (SP-PEG5K)$_6$-Hb (Acharya et al., 2003). The molecular radius of the two new Hb-PEG conjugates are closer to that of previously described Tetra PEGylated (PEG-5K) dog Hb than to that of (SP-PEG5K)$_6$-Hb. The colloidal osmotic pressure of 4 g % solution of the two products are around 35 mm Hg, as compared to the value of 74 mm Hg for a 4 g % solution of (SP-PEG5K)$_6$-Hb.

The iodoacetamide PEG5K used in the present study introduces only an alkyl(methyl) chain on the sulfur atom of the new thiol groups of the thiolated protein and the PEG. Iodoacetamide chemistry based PEG reagents can also be used to introduce carboxamide-PEG chains on the α-amino groups and the thiol groups of Cys-93(β) of HbA without changing the net charge on the functional groups PEGylated (conservative PEGylation), i.e. by carrying out the PEGylation reaction with carboxamide-PEG 5K in the absence of iminothiolane.

TABLE 1

Molecular Properties of Conservatively PEGylated Hb

|  | Hb | CAM-PEG5K-Hb | SP-PEG5K-Hb | (SP-PEG-5K)$_6$-Hb |
|---|---|---|---|---|
| Molecular Radius (nm) | 3.0 | 5.4 | 5.2 | 6.5 |
| Retention time (min) (Superose 12) | 62 | 52 | 52 | 50 |
| Colloidal osmotic pressure (mm Hg) | 8 | 34 | 37 | 74 |

III. Effect of IntraMolecular Crosslinks on Molecular Properties of PEG-Hb Conjugate Materials and Methods Reductive Alkylation of HbA with PEG5K-Aldehyde.

Human adult hemoglobin (HbA) was purified from human erythrocytes as previously described (Manjula and Acharya, 2003). αα-crosslinking HbA (αα-HbA) was prepared as previously described (Chatterjee et al., 1986). Cys-93-ββ-succinimidophenyl polyethylene glycol 2000 hemoglobin A (ββ-crosslinking HbA, ββ-HbA) was prepared as described by Manjula et al. (2000). HbA, αα-HbA and ββ-HbA (0.25 mM tetramer) in 50 mM BisTris-Ac buffer (pH 6.5) were reacted with 10 mM methoxy polyethylene glycol 5000 propionaldehyde (PEG5K-aldehyde, Shearwater Polymers, Huntsville, Ala.) in the presence of 50 mM sodium cyanoborohydride (Sigma Chemical Co., St. Louis, Mo.) at 4° C. overnight. For analytical reactions, the reaction mixture was dialyzed extensively against PBS, pH 7.4 and the product examined by size exclusion chromatographic (SEC) and RPHPLC analysis. For the preparative reactions, the reaction mixture was subjected to diafiltration through a 70-kDa membrane vs. PBS (pH 7.4) using a Minim Tangential Flow Filtration instrument (Pall Corporation, Ann Arbor, Mich.) to remove unreacted PEG and other excess reagents. The final product in the retentate was concentrated and stored frozen at −80° C.

Dynamic Light Scattering.

Dynamic light scattering for molecular radius measurement was performed using a DynaPro instrument (Protein Solutions, Lakewood, N.J.). Samples at the protein concentration of 1 mg/ml were centrifuged at 13,000 rpm for 4 min prior to analysis.

Colloidal Osmotic Pressure Measurements.

A Wescor 4420 Colloidal Osmometer was used to measure the colloidal osmotic pressure of the HbA samples. The measurements were performed using a series of concentrations of HbA samples in PBS (pH 7.4) and at room temperature. Osmocoll reference standards were used to calibrate the instrument before measurements of the samples.

Viscosity Measurements.

The viscosity of the Hb samples was measured with a cone and a rheometer at a protein concentration of 40 mg/ml. A series of concentrations of HbA samples were measured using the cone spindle (CPE-40, Brookfield) at a shear rate of 75 per second in PBS (pH 7.4) and at 37° C.

Analytical Methods.

Determination of the PEGylation induced size enhancement of Hb by size exclusion chromatography (SEC) on Superose 12 columns, RPHPLC analysis of globin chains on a Vydac C4 column (4.6×250 mm), and SDS-PAGE analysis were carried out as previously described (Manjula et al., 2003; Rao et al., 2003). Isoelectric focusing electrophoresis (IEF) was operated using precast resolve gels from Isolab and a blend of pH 6-8 resolve ampholytes. Gels were electrofocused for 3 h to resolve the components in the sample completely. Oxygen-binding equilibrium measurements were carried out using a Hemox Analyzer as described by Cheng et al. (2002).

Tryptic Peptide Mapping.

Tryptic peptide mapping of the PEGylated Hb was carried out by methods previously described (Doyle et al., 1999; Lippincott et al., 1997). The tryptic peptides were analyzed by RPHPLC on a Vydac C18 column (10 mm×250 mm) using a linear gradient of 5-50% acetonitrile containing 0.1% TFA in 160 min, followed by a linear gradient of 50-70% acetonitrile-0.1% TFA in 20 min. The flow rate was 2 ml/min and the effluent was monitored at 210 nm. Percent modification of the amino acid residues modified in the PEGylated Hb was evaluated essentially as described by Lippincott et al. (1997) and Doyle et al. (1999). Briefly, the recovery of peptide βT4 was used as an internal standard, and the ratio of the peak area of each peptide of the PEGylated Hb and PEGylated αα-Hb relative to the corresponding peak in the HbA and αα-Hb peptide map, respectively, was used to elucidate the amino acid residues modified by PEGylation.

Analytical Ultracentrifugation.

Sedimentation velocity measurements were conducted in a Beckman XL-I analytical ultracentrifuge in PBS buffer at pH 7.4, 25° C. and 55,000 rpm. Boundary movement was followed at 405 nm using the centrifuge's absorption optics. For each sample, data were collected at three concentrations ($A_{405}$=0.1, 0.5 and 1.0). The g(s*) distributions were determined using DCDT+ version 2.0.4 (http://www.jphilo.mailway.com) using values of $\bar{v}$ of 0.74 mL/g for HbA (Kellet, 1971) and 0.806 mL/g for the PEGylated proteins (Dhalluin et al., 2005) and normalized to standard conditions ($S_{20,W}$ and $D_{20,W}$) by correcting for buffer density and viscosity.

Circular Dichroism Spectroscopy.

Circular dichroism spectra of Hb samples were recorded on a JASCO-720 spectropolarimeter (JASCO, Tokyo, Japan) at 25° C. with a 0.2-cm light path cuvette (310 µl). For the spectra from 250 to 200 nm, the Hb concentration was 1.3 µM as tetramer. For the spectra from 480 to 250 nm, the Hb concentration was 26.0 µM as tetramer. All the Hb samples were in PBS, pH 7.4. The molar ellipticity, θ, is expressed in deg.cm$^2$/dmol on a heme basis.

Fluorescence Measurements.

Intrinsic fluorescence measurements of Hb samples were performed using Shimadzu RF-5301 spectrofluorimeter at room temperature. The emission spectra were recorded from 295 to 400 nm using an excitation wavelength of 280 nm. Excitation and emission slit widths were both 5 nm. All the samples used were at Hb concentration of 1 mg/ml in PBS, pH 7.4. Cuvette with 1 cm path-length was used.

Results

Influence of αα-Fumaryl Intramolecular Crosslink on the Site Selectivity and Extent of PEGylation of Hb.

The sites of PEGylation as well as the extent of PEGylation of αα-Hb has been established by comparing the tryptic peptide maps of unmodified αα-Hb with that of its PEGylated product. These results have been compared with that of PEGylation of unmodified Hb. As presented in Table 2, Val-1(α) and Val-1(β) have been completely modified by PEGylation in αα-fumaryl-Hb just as in the control uncross-linked Hb. Besides these two major sites of PEGylation in the PEGylated αα-Hb, four lysine residues also showed modification by PEGylation comparable to those of uncross-linked proteins and these sites of partial modification (PEGylation) are also same as those in the uncrosslinked sample (Hu et al., 2005). Thus it is clear that the presence of intramolecular αα-fumary crosslink within the central cavity of Hb has essentially very little influence on the site selectivity of the reductive alkylation chemistry based PEGylation of the protein. Besides, the αα-crosslinked Hb has also been PEGylated to the same level of uncrosslinked Hb. Accordingly PEGylated αα-Hb is referred to (Propyl-PEG5K)$_6$-αα-Hb, in conformity with the earlier nomenclature of hexaPEGylated Hb generated by the same PEGylation chemistry as (Propyl-PEG5K)$_6$-Hb.

Electrophoretic Analysis of (Propyl-PEG5K)$_6$ αα-Hb.

As shown by SDS-PAGE analysis (FIG. 2A), the electrophoretic pattern for HbA is a doublet corresponding to its α and β chain (Lane 2). The α chain of αα-Hb showed a slower mobility as a consequence of cross-linkage (Lane 3). On PEGylation, the doublet corresponding to the unmodified globin chains disappears, and displays two major protein bands with slower mobility relative to the unmodified globin chains and two minor bands that exhibit even slower mobility relative to the two major bands (Lane 5). For (Propyl-PEG5K)$_6$-αα-Hb (Lane 4), the two major bands of (Propyl-PEG5K)$_6$-Hb became lighter with the concomitant appearance of two new bands with slower mobility. Iodine stain of the electrophoresis gel to locate the PEGylated products showed that stain intensity is comparable with different bands between the two PEGylated proteins. This suggests that the labeling of the two chains of Hb with PEG-chains is comparable. This is consistent with the results of the tryptic peptide mapping of the two PEGylated proteins.

Figures 2A, 2B:
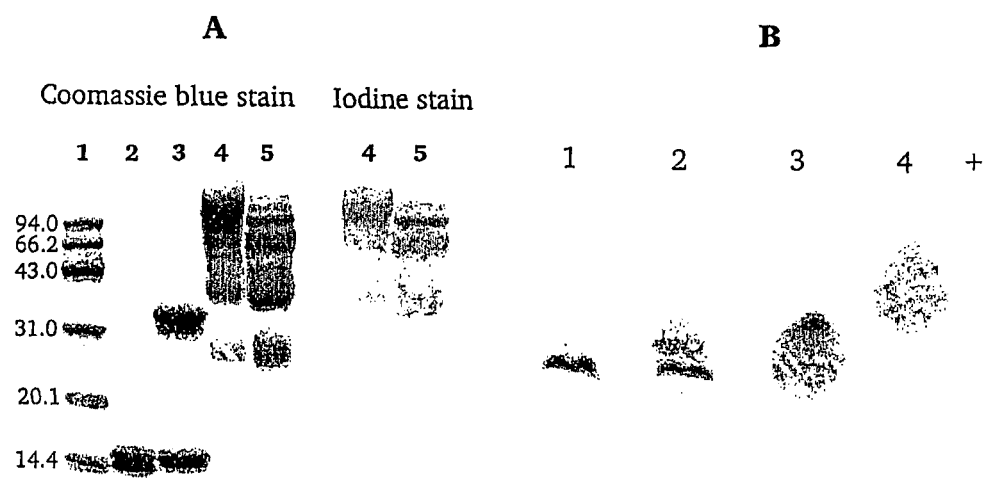
FIG. 2A-2B. Characterization of (Propyl-PEG5K)$_6$-Hb and (Propyl-PEG5K)$_6$-αα-Hb by SDS-PAGE (A) and isoelectric focusing (IEF) (B). A: SDS-PAGE was carried out on a precast 14% tris-glycine gel from the Invitrogen Corporation. Lane 1, molecular weight markers; Lane 2, HbA; Lane 3, αα-Hb; Lane 4, (Propyl-PEG5K)$_6$-αα-Hb; and Lane 5, (Propyl-PEG5K)$_6$-Hb. B: IEF was operated using precast resolve gels from Isolab and a blend of pH 6-8 resolve ampholytes. Lane 1, HbA; Lane 2, αα-Hb; Lane 3, (Propyl-PEG5K)$_6$-Hb; and Lane 4, (Propyl-PEG5K)$_6$-αα-Hb.

The influence of the intramolecular crosslinking on the isoelectric focusing (IEF) pattern of the PEGylated proteins is shown in FIG. 2B. The PEGylated proteins do not focus as compact bands, and are thus distinct from HbA and αα-Hb. (Propyl-PEG5K)$_6$-Hb focused slightly behind HbA. Besides, (Propyl-PEG5K)$_6$-αα-Hb focused slightly behind (Propyl-PEG5K)$_6$-Hb. Since the reductive alkylation chemistry based PEGylation of Hb is not expected to influence the net positive charge of the surface amino groups to which the PEG-chains are conjugated, it is suggested that the influence of PEGylation on the IEF pattern reflects the molecular shielding influence of the PEG-shell on the surface charges of Hb from the bulk solvent (Doyle et al., 1999). Since HbA and αα-fumaryl Hb exhibit similar isoelectric patterns, the molecular shielding influence of the PEG-shell on the surface charges of tetramer may be enhanced with (Propyl-PEG5K)$_6$-αα-Hb relative to that in (Propyl-PEG5K)$_6$-Hb.

Higher Hydrodynamic Volume of (Propyl-PEG5K)$_6$-αα-Hb as Compared to that of (Propyl-PEG5K)$_6$-Hb by Size Exclusion Chromatography.

Figure 3:
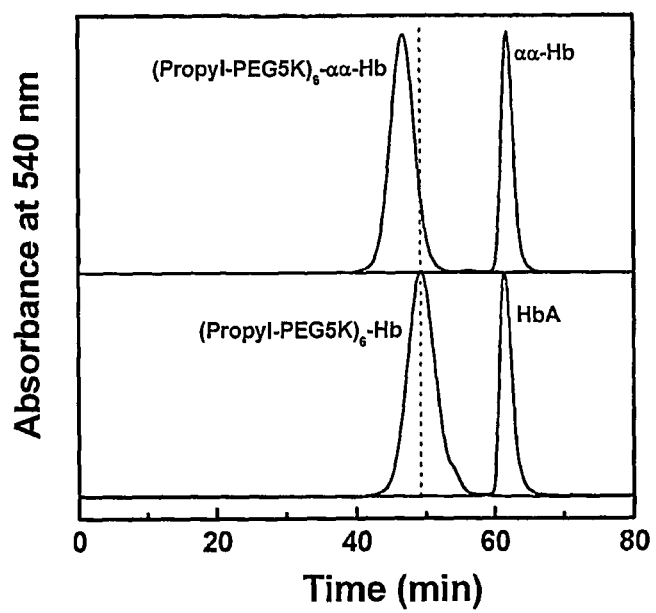
FIG. 3. Size exclusion chromatographic analysis of PEGylated Hb samples. The analysis was carried out at room temperature on two HR10/30 Superose 12 columns (Amersham-Pharmacia Biotech) connected in series. The column was eluted with PBS, pH 7.4 at a flow rate of 0.5 ml/min, and the effluent was monitored at 540 nm.

The molecular volume of the two PEGylated forms of Hb (crosslinked and uncrosslinked) have been compared by size exclusion chromatography (SEC) on Superose 12 column. In the lower panel of FIG. 3, the SEC patterns of HbA and its hexaPEGylated form generated by reductive alkylation form is presented. FIG. 3, upper panel, compares the SEC patterns of αα-fumaryl Hb and its hexaPEGylated form. The hexaPEGylation of HbA results in an earlier elution of the protein reflecting a significant increase in the hydrodynamic volume of Hb. The SEC pattern of HbA is not influenced by the presence of αα-fumaryl intra molecular crosslinks. On hexaPEGylation of αα-fumaryl-Hb under the same reaction condition as that used for HbA, hydrodynamic volume of cross-linked Hb is significantly increased, much more than that of PEGylation of uncrosslinked HbA as reflected by the earlier elution of (Propyl-PEG5K)$_6$ αα-Hb as compared to (Propyl-PEG5K)$_6$-Hb. Based on the results of tryptic mapping (Table 2), it is evident that the larger increase in the hydrodynamic volume of αα-fumaryl Hb compared to uncrosslinked HbA is not related to the higher level of PEGylation or an altered site selectivity of PEGylation. Thus αα-fumaryl intra-molecular cross-link in Hb appears to increase the propensity of PEGylation to induce higher hydrodynamic volume. It has been previously noted that the hexaPEGylated Hb exhibits a hydrodynamic volume comparable to that of an oligomeric form of intramolecularly crosslinked Hb that carries four tetrameric units. Thus the molecular volume of (Propyl-PEG5K)$_6$-αα-Hb is higher than that of such oligomeric Hbs that carry four copies of intramolecular crosslinked Hbs.

Molecular Volume of (Propyl-PEG-5K)$_6$-αα-fumaryl Hb as Determined by Dynamic Light Scattering.

The molecular radius of the various products, as determined by dynamic light scattering and their calculated molecular volume are summarized in Table 3. The molecular radius of the αα-fumaryl Hb is comparable to that of HbA, a result that parallels the SEC studies (FIG. 3). As reported earlier, (Propyl-PEG5K)$_6$-Hb showed a molecular radius of 5.40 nm, reflecting the enhanced molecular dimensions of the PEGylated Hb. Interestingly, the molecular radius of (Propyl-PEG5K)$_6$-αα-Hb exhibits further increase in the molecular radius as compared to (Propyl-PEG5K)$_6$-Hb, which lacks the αα-fumaryl crossbridge. The calculated molecular volume of (Propyl-PEG5K)$_6$ αα-Hb is nearly twice that of (Propyl-PEG5K)$_6$-Hb. These results are consistent with the data from SEC, and quantifies the data on increase in molecular volume.

Influence of PEG-Chain Length on the Molecular Volume of (Propyl-PEG)$_6$ αα-Hb.

PEG2K-aldehyde and PEG20K-aldehyde are lower and higher homologues of the PEG5K-aldehyde, respectively. To establish the effect of PEG-chain length on the influence of αα-fumaryl crosslink on the enhanced efficiency of PEGylation induced increase in the molecular volume Hb, the reductive alkylation of Hb with PEG-aldehyde has been studied using PEG-2K aldehyde and PEG-20K aldehyde.

Figures 4A, 4B:
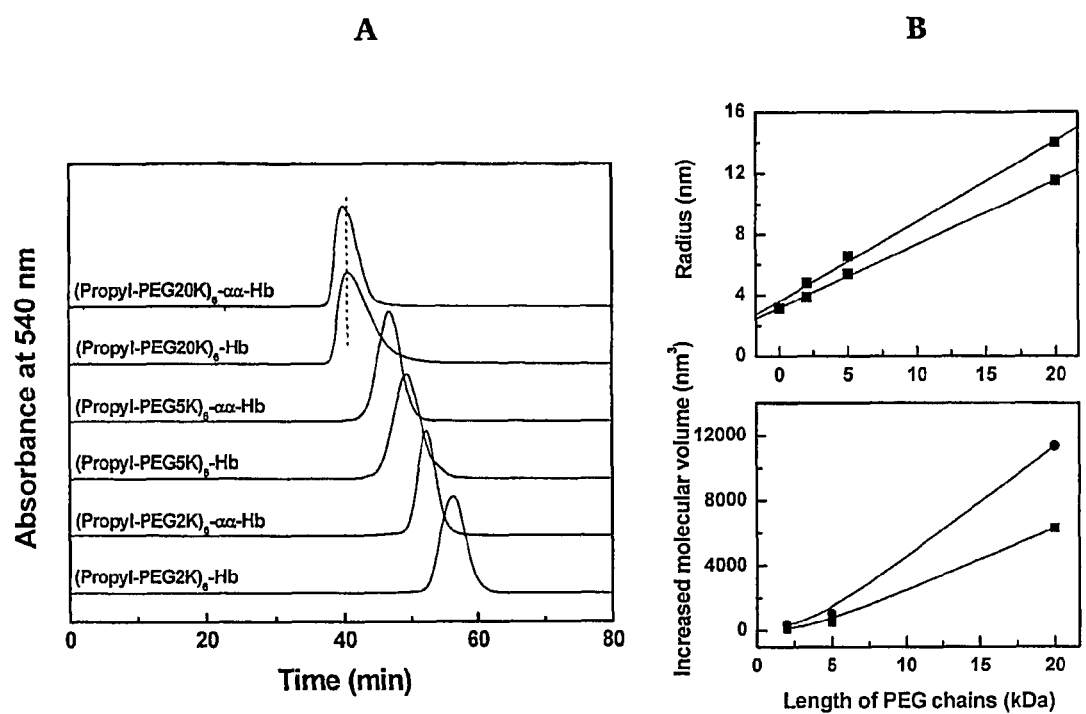
FIG. 4A-4B. Influence of PEG-chain length on the molecular volume of (Propyl-PEG)$_6$ αα-Hb. A: Size exclusion chromatographic analysis of PEGylated protein. The analysis was carried out at room temperature on two HR10/30 Superose 12 columns connected in series. The column was eluted with PBS, pH 7.4 at a flow rate of 0.5 ml/min. B: Size enhancement of Hb as a function of the length of attached PEG chains. Molecular radii were measured by dynamic light scattering at a protein concentration of 1 mg/ml. ΔV was calculated with an equation $\Delta V = 4\pi(R^3 - R_0^3)/3$. R and $R_0$ are radii of PEGylated Hbs and HbA, respectively.

The hydrodynamic volume of the PEGylated products generated from uncrosslinked and crosslinked Hb has been compared using SEC (FIG. 4A). The reductively alkylation mediated PEGylation of αα-fumaryl Hb generated using PEG2K-aldehyde as well as that generated using PEG-20K aldehyde exhibited higher hydrodynamic volume as compared to the respective PEGylated product generated from uncrosslinked Hb.

FIG. 4B compares the increase in the molecular radius of Hb on PEGylation using reductive alkylation chemistry as a function of PEG-chain length. Thus this reflects the influence of αα-fumaryl crosslinks on increase in the molecular volume resulting from PEGylation. As the chain length of the PEG is increased, the difference in the molecular radius between the PEGylated products of crosslinked and uncrosslinked protein is also increased. The hydrodynamic volumes of the three PEGylated Hbs generated from αα-fumaryl Hb is nearly twice that of the corresponding PEGylated Hb. Therefore, the influence of αα-fumaryl intramolecular crosslink to increase the propensity of PEGylation to enhance molecular volume of Hb is correlated with the chain length of the PEG-aldehyde used for reductive alkylation; it reflects the size of the PEG-shell.

Influence of αα-Fumaryl Crossbridge on the Viscosity and Colloidal Osmotic Pressure of HexaPEGylated Hb.

Figure 5:
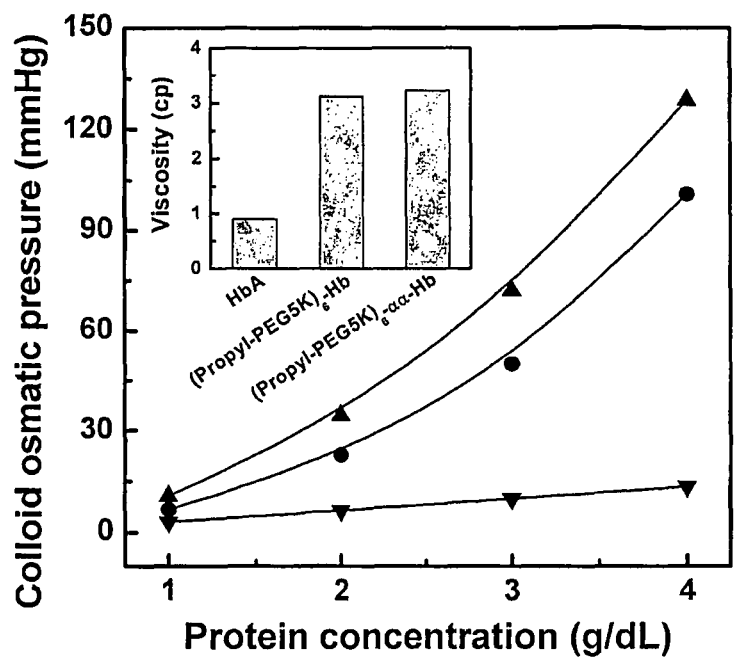
FIG. 5. Colloidal osmotic pressures of HbA (■), (Propyl-PEG5K)$_6$-Hb (●), (Propyl-PEG5K)$_6$-αα-Hb (▲) as a function of protein concentration. A series of concentrations of HbA samples were measured by a Wescor 4420 Colloidal Osmometer in PBS (pH 7.4) and at room temperature. The inset indicated the comparison of the viscosity of (Propyl-PEG5K)$_6$-αα-Hb with that of (Propyl-PEG5K)$_6$-Hb at 4 g/dL.
Figure 6:
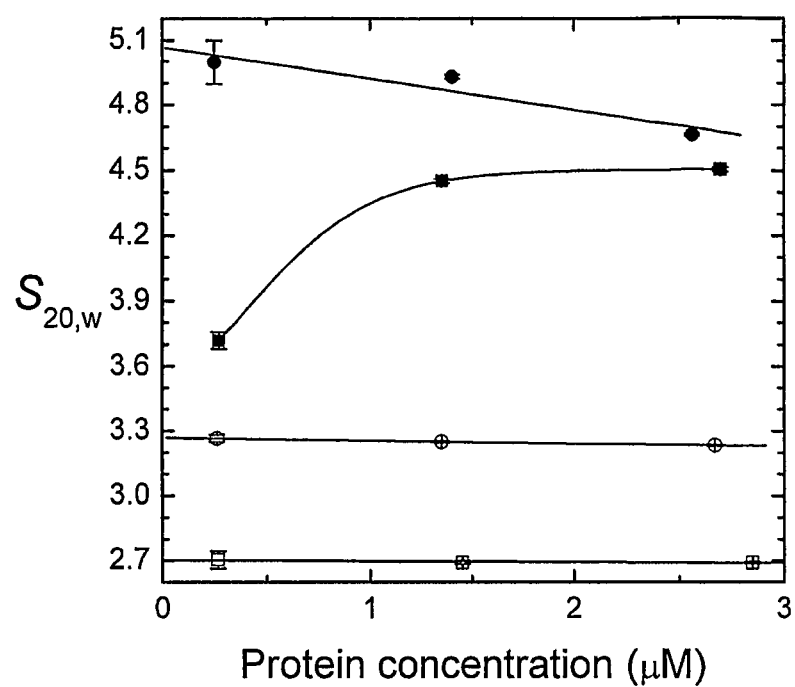
FIG. 6. $S_{20,W}$ of PEGylated proteins as a function of hemoglobin concentrations. Sedimentation velocity measurements of (Propyl-PEG5K)$_6$-Hb (□), (Propyl-PEG5K)$_6$-αα-Hb (○), HbA (■) and αα-Hb (●) were conducted in a Beckman XL-I analytical ultracentrifuge in PBS buffer at pH 7.4, 25° C. and 55,000 rpm. Boundary movement was followed at 405 nm using the centrifuge's absorption optics.

PEGylation induced (i) enhanced molecular volume (ii) viscosity and (iii) colloidal osmotic pressure are the three important parameters that are critical for the neutralization of vasoactivity. In view of the influence of αα-fumaryl intra molecular crosslinking on the molecular radius of the PEGylated Hb, its influence on viscosity and COP has also been investigated and compared with that of hexaPEGylated derivative generated using αα-fumaryl Hb. FIG. 5 shows the correlation of COP of (Propyl-PEG5K)$_6$ αα-Hb with protein concentration. As with the other PEGylated samples studied earlier, the COP of (Propyl-PEG5K)$_6$-ααHb exhibits a non-linear dependence on the protein concentration (FIG. 6). The COP of a sample reflects the number of particles in solution. (Propyl-PEG5K)$_6$-αα-Hb exhibited lower COP value as compared to the (Propyl-PEG5K)$_6$-Hb in spite of its larger molecular volume. The lower value of COP for the solutions of (Propyl-PEG5K)$_6$-αα-Hb is for the entire range of the protein concentration.

The viscosity of (Propyl-PEG5K)$_6$-αα-Hb at a protein concentration of 40 mg/ml has been compared with that of HbA and (Propyl-PEG5K)$_6$-Hb and the results are presented as an inset in FIG. 5. The PEGylation induced increase in the viscosity of Hb is not influenced much by the αα-fumaryl intra molecular crossbridge.

Thus the presence of αα-fumaryl crossbridge (i) nearly doubles the PEGylation induced hydrodynamic volume and (ii) lowers the PEGylation induced colloidal osmotic pressure by about 30%, but has very little influence on the PEGylation induced viscosity when compared with the PEGylation induced changes in the molecular properties of uncrosslinked Hb. These influences seen as a consequence of intramolecular crosslinks could be explained on the basis of an increase in the dissociation of uncrosslinked Hb as a result of PEGylation as compared to that with the uncrosslinked Hb.

Analytical Ultracentrifugation Studies.

PEGylated samples as well as the starting crosslinked and uncrosslinked materials have been subjected to analytical ultracentrifugation studies to gain more insight into the influence of PEGylation on the inter dimeric interactions of Hb. The samples have been subjected to sedimentation velocity analysis (FIG. 6). The decrease in sedimentation coefficient (S) values observed for (Propyl-PEG5K)$_6$-αα-Hb with increasing protein concentration is characteristic of a stable monodisperse particle (●). The estimated M$_w$ of this particle from S°$_{20,w}$/D°$_{20,w}$ is ~90 kDa, consistent with a hexaPEGylated tetramer. In contrast, the sedimentation rate of (Propyl-PEG5K)$_6$-Hb is much slower, displaying a slight decrease in sedimentation with increasing protein concentration that lacks self-association (○). The estimated M$_w$ of this particle is ~60 kDa consistent with a predominant presence of PEGylated dimers. As a control, native and crosslinked HbA was analyzed under identical experimental conditions. Crosslinked HbA also sediments as a stable monodisperse particle (●); the estimated M$_w$ of ~55 kDa is consistent with a tetramer. In contrast, native HbA shows its well-documented dimer-tetramer association (○). Comparison of the non-crosslinked Hb molecules indicates that PEGylation destabilizes the Hb tetramer. In addition, S$_{20,w}$ values of (Propyl-PEG5K)$_6$-Hb and (Propyl-PEG5K)$_6$-αα-Hb are lower than those of HbA and αα-Hb, indicating that the PEG-moiety can be envisaged as a 'parachute' slowing down the sedimentation rate (Dhalluin et al., 2005).

Influence of αα-Fumaryl-Intra Molecular Crossbridge on Structural Features of (Propyl-PEG5K)$_6$-Hb: (i) CD Measurements.

Figures 7A, 7B:
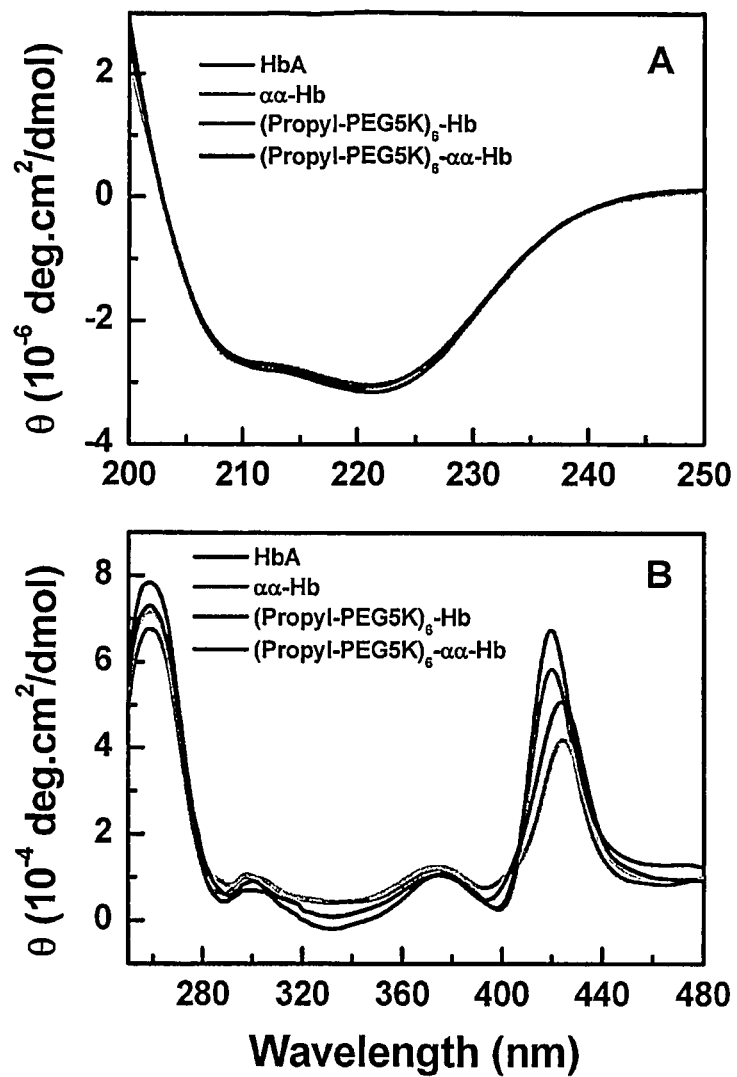
FIG. 7A-7B. Circular dichroism spectra of PEGylated proteins. Circular dichroism spectra of Hb samples were recorded at 25° C. with a 0.2-cm light path cuvette (310 μl) in far-UV region (200-250 nm, A), near-UV and Soret region (250-480 nm, B), and visible region (480-650 nm). The molar ellipticity, θ, is expressed in deg.cm$^2$/dmol on a heme basis.

Possible differences between the structural features of (Propyl-PEG5K)$_6$-Hb and (Propyl-PEG5K)$_6$-αα-Hb have been investigated using circular dichroism spectroscopy. The far-UV (absorbance 200-250 nm) CD spectra for the PEGylated proteins were shown in FIG. 7A. As indicated by the ellipticity values at 222 nm, the α-helical content of HbA was not changed upon the introduction of αα-cross-bridge and/or PEGylation. Thus, the secondary structure of the chains of HbA has not been influenced significantly either by αα-cross-linking or on subsequent PEGylation.

In the near-UV CD region (FIG. 7B), the L-band (centered around 260 nm) is considered to be sensitive to the interactions between the heme and the surrounding globin, being influenced by the attached ligand (Zentz et al., 1994). PEGylation of HbA induced the increase in the intensity of L band, while PEGylation of αα-Hb showed no change in the ellipticity of this band. This indicated that the increased intensity of L band of HbA upon PEGylation was not related to PEGylation itself, but related to PEGylation induced structural changes of HbA, tetramer dissociation. The region around 285 nm is considered as indicative of the R to T transition, and correlated to the environment of α42 and β37 aromatic residues in human HbA (Perutz et al., 1974). PEGylation of HbA and αα-Hb both induced a decrease in the ellipticity around 285 nm associated with higher oxygen affinity (R state) (Perutz et al., 1974). This is possibly due to the PEGylation induced conformational change around α42 and β37. This region reflects the α1β2 subunit interface contact domain. Thus, the PEG shell of the PEGylated Hb appears to reduce the propensity of the molecule to transition from R to T state, and this is consistent with the fact that PEGylation increases the oxygen affinity of Hb.

Most significant changes were noticed in the soret band region of the CD spectra. The Soret region the spectra of Hb is informative on the interactions of heme prosthetic group with the surrounding aromatic residues and to modifications in the spatial orientation of these amino acids with respect to heme, affecting porphyrin transitions and π-π* transitions in the surrounding aromatic residues (Hsu and Woddy, 1971). The presence of the αα-fumaryl intramolecular crossbridge reduces the intensity of the Soret band of HbA with a wavelength shift to the red. This represents the presence of deoxy like features in the crosslinked Hb (Perutz et al., 1974). The PEGylation of Hb to generate (Propyl-PEG5K)$_6$-Hb increases the intensity of the soret band without noticeable changes in the wavelength. This reflects that the microenvironment of heme is slightly perturbed upon PEGylation (Hu et al., 2005). The presence of αα-crosslinks in the hexaPEGylated samples increases slightly the intensity of the band just as in the case of uncrosslinked Hb, but the intensity is significantly lower than that of the hexaPEGylated sample without the intramolecular crosslinks. The red shift in the soret band induced as a result of the ααcrosslinking is conserved even on PEGylation, which is considered as the reflection of the lower affinity of heme for oxygen (Perutz et al., 1974).

Influence of αα-Fumaryl-Intra Molecular Crossbridge on Structural Features of (Propyl-PEG5K)$_6$-Hb: (ii) Fluorescence Measurements.

Figure 8:
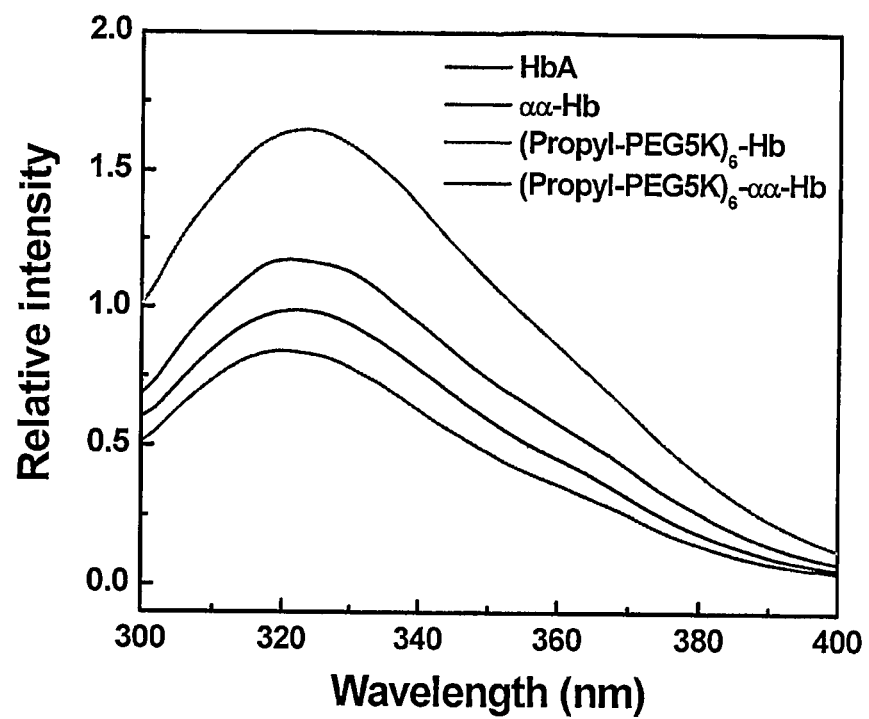
FIG. 8. Intrinsic fluorescence emission spectra of HbA, αα-Hb, (Propyl-PEG5K)$_6$-Hb and (Propyl-PEG5K)$_6$-αα-Hb. The excitation wavelength was 280 nm. The measurements were performed using Shimadzu spectrofluorimeter at room temperature. All the samples used were at Hb concentration of 1 mg/ml in PBS, pH 7.4.

Intrinsic fluorescence of Hb is primarily due to the fluorescence of β37Trp at the α1β2 interface, which reflects the stability of the quaternary structure of Hb (Hirsch, 2003). As can be seen in FIG. 8, when excited at 280 nm, HbA and αα-Hb showed similar fluorescence emission intensity with a peak position at 320 nm. (Propyl-PEG5K)$_6$-αα-Hb also showed comparable emission intensity to HbA and αα-Hb, indicating that the attachment of PEG chain did not alter the quaternary interactions of Hb. However, fluorescence intensity of (Propyl-PEG5K)$_6$-Hb is significantly higher as compared to (Propyl-PEG5K)$_6$-αα-Hb and exhibits a noticeable blue shift, and reflects the perturbation of the quaternary structure. In conjunction with the ultracentrifugal studies, this may be reflective of the enhanced dissociation of the tetramers (reflection of the presence of dimers), and inhibition of such dissociation by intramolecular αα-fumaryl cross bridges.

Influence of Engineering ββ'-Succunimidophenyl PEG-2000 Intramolecular Cross-Bridge on the Molecular Properties of (Propyl-PEG5K)$_6$-Hb.

The αα-crosslinkage engineered into (Propyl-PEG5K)$_6$-Hb is a central cavity intra molecular crosslink. The central cavity of Hb plays a dominant role in dictating the structural stability and functional properties of Hb. The influence of the αα-fumaryl crossbridge on the molecular properties of (Propyl-PEG-5K)$_6$-Hb may be unique as it is an αα-crosslink or it is a within the central cavity cross-bridge. In an attempt to establish the fact that the observed influence on the molecular properties of (Propyl-PEG-5K)$_6$-Hb is a consequence of an intra molecular crossbridge that prevents the dissociation of the tetramers into dimers, the effect of a crosslink outside the central cavity of Hb was investigated. Bβ'-succinimidophenyl PEG-2000 crosslink has been also engineered into (Propyl-PEG5K)$_6$-Hb to provide an answer to this question. As can be seen in Table 4, the presence of ββ-succinimidophenyl PEG-2000 crosslink in (Propyl-PEG5K)$_6$-Hb nearly parallels the influence of introducing the intramolecular αα-fumaryl into (Propyl-PEG5K)$_6$-Hb. The molecular radius and the hydrodynamic volume are increased, there is limited influence on viscosity, and the COP of (Propyl-PEG5K)$_6$-Hb decreased upon ββ-crosslinkage. Therefore, ββ-crosslinking of (PropylPEG5K)$_6$-Hb also achieves the same results as the αα-crosslinking, apparently by preventing the PEGylated molecule from dissociating into dimers as a consequence of weakened interaction between the interdimer interactions.

TABLE 2

Sites of PEGylation in αα-fomaryl HbA

| Residue modified | Percent modification | |
|---|---|---|
| | (Propyl-PEG5K)$_6$-Hb | (Propyl-PEG5K)$_6$-αα-Hb |
| Val-1(α) | 100 | 100 |
| Val-1(β) | 100 | 100 |
| Lys-8(β) | 23 | 23 |
| Lys-11(α) | 23 | 27 |
| Lys-40(α) | 12 | 11 |
| Lys-56(α) | 17 | 22 |

The sites of PEGylation in the PEGylated proteins are determined by tryptic peptide mapping of their globin chains as described previously.

TABLE 3

Molecular Radius of (Propyl-PEG5K)$_6$ αα-Hb

| Sample | Radius (nm) | Volume (nm³) |
|---|---|---|
| HbA | 3.14 | 129.6 |
| αα-Hb | 3.16 | 132.1 |
| ββ-Hb | 3.35 | 157.4 |
| (Propyl-PEG5K)$_6$-Hb | 5.40 | 659.2 |
| (Propyl-PEG5K)$_6$-ααHb | 6.56 | 1181.9 |
| (Propyl-PEG5K)$_6$-ββ-Hb | 6.70 | 1259.2 |

The protein samples at a concentration of 1 mg/ml were centrifuged at 13,000 rpm for 4 min prior to analysis.

TABLE 4

Comparison of the Solution properties of Hexa PEGylated Hbs

| | Molecular | | | |
| | Radius (nm) | Volume (nm³) | COP (mmHg) | Viscosity (cp) |
|---|---|---|---|---|
| (Propyl-PEG5K)$_6$-Hb | 5.40 | 659.2 | 128.5 | 3.11 |
| (Propyl-PEG5K)$_6$-αα-Hb | 6.56 | 1181.9 | 100.8 | 3.23 |
| (Propyl-PEG5K)$_6$-ββ-Hb | 6.70 | 1259.2 | 85.2 | 2.97 |

The viscosity and COP were measured at a Hb concentration of 4 g %. Samples at the protein concentration of 1 mg/ml were centrifuged at 13,000 rpm for 4 min prior to analysis.

Figure 9:
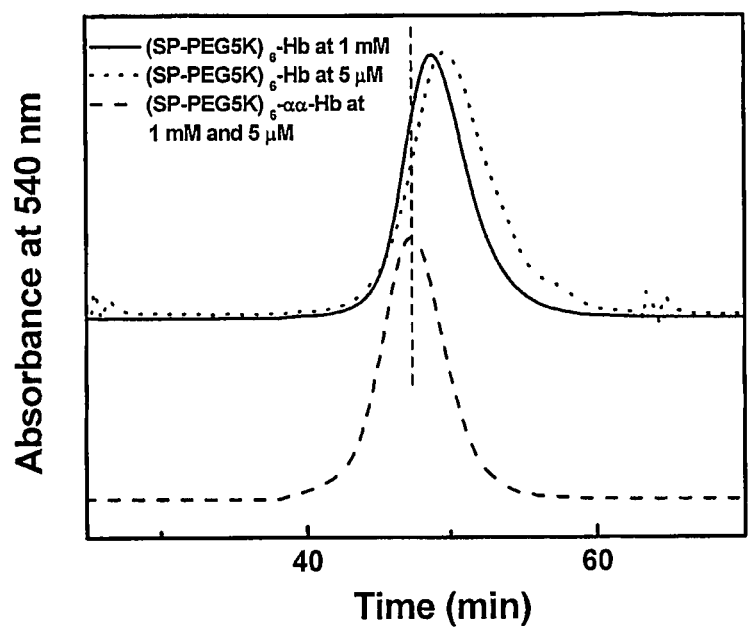
FIG. 9. Comparison of the SEC chromatography of the hexaPEGylated Hb generated from uncrosslinked and alpha alpha fumaryl Hb.

Extension Arm Facilitated, Maleimide Chemistry Based PEGylation of ββ-Succinimodo Phenyl PEG-2000 Hb.

ββ-succinimido phenyl PEG-2000 Hb (an intramolecularly crosslinked Hb) was PEGylated using the thiolation mediated PEGylation. Its properties were compared with those of a nonhypertensive hexaPEGylated Hb generated using extension arm facilitated PEGylation of uncrosslinked Hb using maleimide-PEG (Table 5). In PEGylated ββ-succinimido phenyl PEG-2000 Hb, Cys-93(β) is involved in intramolecular crosslinking, and hence not available for PEGylation. Apparently the site selectivity of PEGylation in the crosslinked and uncrosslinked is slightly different (and the extent of PEGylation could be slightly lower). The molecular properties presented here show that at 4 gm % level, the extent of dissociation of PEGylated Hb is not as significant as that seen in the PEGylated product generated by reductive alkylation protocol. Accordingly, to establish this aspect further, αα-fumaryl Hb has been subjected to thiolation mediated PEGylation according to the procedures described earlier. In this crosslinked Hb, Cys-93(β) is accessible for reaction of PEG-maleimide and hence the site selectivity of the product is expected to be comparable. As seen in the Table 5, the molecular radius of the product generated from crosslinked Hb is slightly higher. A comparison of the size exclusion chromatography of the PEGylated crosslinked product and PEGylated uncrosslinked product as a function of the protein concentration (1 mM and 5 μM) has demonstrated that the product generated by the thiolation mediated maleimide chemistry based PEGylation using the crosslinked Hb is larger than the product generated from the uncrosslinked Hb. But the difference is smaller than that seen with the reductive alkylation product (FIG. 9). Thus one can conclude that PEGylation of uncrosslinked Hb increased the dissociation of Hb.

With the contemplated use of hexaPEGylated product at 4 gm %, there will be considerable in vivo dilution of this sample, and the amount of dissociated species in circulation is likely to be higher depending on the final concentration of Hb in the plasma as compared to the amount in the transfused solution. A further dilution of Hb concentration in the plasma as a consequence of inflow of liquid to the vascular system (a consequence of the COP of PEGylated Hb) is also anticipated. Therefore, the use of intramolecularly crosslinked Hb is a better choice for generating PEGylated Hb as blood substitutes as compared to the uncrosslinked Hb that has been used earlier.

TABLE 5

Molecular properties of (SP-PEG5K)₆-Hbs

| Sample | Radius (nm) | Volume (nm³) | COP (mmHg) | Viscosity (cp) |
|---|---|---|---|---|
| (SP-PEG5K)6-ββ-succinimidophenyl PEG-2000-Hb | 6.12 | 959.7 | 62.1 | 2.28 |
| (SP-PEG5K)6-αα-fumaryl-Hb | 6.44 | 1118.2 | — | — |
| (SP-PEG5K)6-Hb | 6.06 | 931.7 | 73.9 | 2.50* |
| ββ-succinimidophenyl-PEG-2000 Hb | 3.35 | 157.4 | | |
| αα-fumaryl-Hb | 3.24 | 142.4 | | |
| HbA | 3.10 | 124.7 | | |

*Data is from Manjula et al. (2005)

IV. Conservative PEGylation of Albumin

PEGylated Albumin as a Plasma Volume Expander:

The simplicity of thiolation mediated maleimide chemistry based conservative PEGylation has prompted the translation of the thiolation mediated PEGylation procedure to produce PEGylated albumin in large amounts to facilitate its evaluation as a plasma volume expander. Given the fact that the molecular weight of albumin is comparable to that of Hb, hexaPEGylation of albumin by the thiolation mediated PEGylation using maleimide PEG-5K as the PEG-reagent is likely to generate a species of PEGylated albumin the solutions of which will be iso-hydrodynamic volume, iso-viscosity and iso-colloidal osmotic pressure with hexaPEGylated Hb (Acharya et al., 2003).

Accordingly, thiolation mediated maleimide chemistry based PEGylation of albumin was carried out with maleimide-phenyl-PEG-5000 (Mal-Phe-PEG-5K), using reaction conditions comparable to that used for the PEGylation of Hb to generate non-hypertensive Hb. Albumin has 35 half-cystine residues; all of which except one at position 34 (Cys-34) are involved in intra-molecular disulfide bonds. Therefore, more thiol groups were introduced onto the protein using 2-iminothiolane to facilitate the attachment of Mal-Phe-PEG-5K chains.

Albumin has been subjected to PEGylation under two different reaction conditions to generate two PEGylated products with different levels of PEGylation. For the preparation of both of these samples, the maleimide chemistry based PEGylation was used in the one step mode followed by tangential flow filtration of the PEGylated albumin to remove the excess PEG reagent. For the first preparation, reaction conditions were optimized to generate a product with an average of six PEG-chains per molecule as determined by the mass spectral analysis. The hydrodynamic volume of the hexaPEGylated albumin is slightly larger than that of hexa PEGylated Hb. This hexa-PEGylated albumin, (SP-PEG5K)₆-albumin, exhibits a viscosity of 2.4 cp and a colloidal osmotic pressure of 37 mm Hb. Thus, the viscosity of a 4 g % solution of hexa-PEGylated albumin is slightly lower than that of a 4 g % solution of hexa-PEGylated Hb [(SP-PEG5K)₆-Hb]. But the colloidal osmotic pressure of a 4 g % solution of (SP-PEG5K)₆-albumin is noticeably lower than that of the hexa-PEGylated Hb.

The molecular mass of Hb and of albumin are nearly identical, but the hydrodynamic volume of albumin is slightly higher than that of Hb as reflected by size exclusion chromatography. The difference in the hydrodynamic volume is consistent with the fact that the molecular radius of albumin as determined by light scattering is around 4.0 nm whereas that of Hb is only around 3.0 nm. Thus, the six copies of PEG-5K chains conjugated to Hb in (SP-PEG5K)₆-Hb by thiolation mediated conservative PEGylation are more efficient in increasing the colloidal osmotic pressure of Hb than the six copies of PEG-5K chains conjugated by the same conjugation chemistry to albumin. Given the difference in the molecular surface area of Hb and albumin, which is a direct consequence of the difference in the molecular radius of the two unPEGylated parent proteins, the results suggest that there is a correlation between the number of PEG-chains of a given molecular mass on a given molecular surface area, i.e., there is a correlation between the density of PEG-units in a given molecular volume and the colloidal osmotic pressure of the PEGylated protein.

Another preparation of PEGylated albumin that carries on an average 12 copies of the PEG-5K chains per mole, [(SP-PEG5K)₁₂-albumin], has also been prepared. On size exclusion chromatography the (SP-PEG5K)₁₂-albumin elutes only slightly ahead of (SP-PEG5K)₆-albumin. Consistent with the presence of higher number of copies of PEG-5K on the molecular surface as compared to that of (SP-PEG5K)₆-albumin, the viscosity and the colloidal osmotic pressure of (SP-PEG5K)₁₂-albumin are higher, being 3.7 cp and 102 mm Hg respectively, for a 4 g % solution. These results suggest that the correlation between the increase in the colloidal osmotic pressure of a protein as a function of the mass of PEG on a given molecular surface is nonlinear and increases in a exponential fashion, while the viscosity of the sample as a function of the PEGylation is more linear.

Influence of PEGylation of Albumin on its Interaction with Potential Small Molecular Weight Drugs:

Besides contributing to 80% of COP of plasma, albumin also acts as a transporter for insoluble fatty acids and therapeutic drugs. The binding of drugs to albumin is very important for their pharmaco-kinetics. Due to this binding, the clearance of drugs is slow and allows use of low dosage of many drugs. This in turn keeps unbound drugs that can interact with a cognate receptor at low levels and minimizes side effects. In order to determine the ligand binding capability of PEGylated albumin, the binding of a therapeutic drug, warfarin has been studied. Warfarin binds to albumin at Site-I binding site that is located in the A domain of the protein. The binding constants for albumin and (SP-PEG5K)₁₂-albumin has been found to be 3.68 and $3.1 \times 10^{-5}$ $M^{-1}$, respectively. Thus, thiolation-mediated PEGylation of albumin does not impair its drug binding capability of site-I.

The propensity of the PEGylation reaction to endow PEGylated albumin with an enhanced molecular radius besides increased viscosity and colloidal osmotic pressure (COP) should lower filtration. Thus, the extravasation seen on transfusion with albumin solutions, particularly in some pathological conditions, should be reduced. Given the increased viscosity and COP, a lower concentration of PEGylated albumin needs to be used (relative to albumin) to maintain the same parameters.

(SP-PEG5K)₆-albumin and (SP-PEG-5K)₁₂-albumin with enhanced molecular size (hydrodynamic volume), viscosity and colloidal osmotic pressure can serve as better plasma expanders than albumin itself, especially under some pathological conditions wherein there is an increase in the leakiness of the blood vessels for albumin causing edema. Since the drug binding activity of these PEGylated albumin are not significantly influenced by PEGylation, these products are expected to function better than other conventional crystalloid or colloidal plasma expanders that are currently in use.

V. Thiocarbmoyl PEG Albumin

Human serum albumin (0.5 mM) in 10 mM phosphate buffer was reacted with 5 mM (10 fold molar excess) of isothiocyanato phenyl PEG 5K at 4° C. either at pH 6.5 or at pH 9.2 overnight. The reaction mixture was subjected to tangential flow filtration against phosphate buffered saline, pH 7.4, to remove the excess PEG reagent. The removal of the PEG reagent from the sample was followed by an FPLC analysis that monitored the absorbance at 210 nm and the refractive index of the effluent. The sample thus generated exhibited a high degree of molecular size homogeneity. The sample generated at pH 6.5 had about four copies of PEG-5K chains while the one generated at pH 9.2 carried nearly 6 to 7 copies of PEG-5K chains.

VI. Surface Decoration of Human Serum Albumin (HSA) with Multiple Copies of Polyethylene Glycol 5000 (PEG5K) Chains: Extension Arm Facilitated Conservative PEGylation The reactivity and accessibility of the surface functional groups of proteins to macromolecular PEG-reagents are the two major factors that influence efficiency of PEGylation of proteins. A thiol-maleimide chemistry based, extension arm facilitated PEGylation protocol has been developed to overcome these limitations and applied to HSA to develop PEGylated HSA as a plasma volume expander. By controlling the concentration of HSA and of iminothiolane (a reagent that engineers the extension arm on surface amino groups with a thiol group at its distal end) the number of copies of PEG-chains coupled to HSA can be controlled, HexaPEGylated HSA has been generated to compare the chemical, biochemical and colligative properties of the material with that of vasoinactive, nonhypertensive hexaPEGylated Hb (Manjula et al., 2005). The one step PEGylation protocol wherein the maleimide PEG is present during thiolation is an improved protocol that avoids formation of thiolation induced oligomerization of HSA during PEGylation. Interestingly, PEGylation induced properties of hexaPEGylated HSA are distinct from those of hexaPEGylated Hb. The lower viscosity and colloidal oncotic pressure and higher hydrodynamic volume of PEGylated HSA compared to the hexaPEGylated HbA at comparable protein concentrations suggests that either the colligative properties of PEGylated protein are a correlate of the density of the PEG-chains on the molecular surface, or hexa PEGylated Hb dissociates to have a higher number of effective particles in solution. The simplicity and cost effectiveness of this PEGylation protocol makes this a candidate for large scale production of PEGylated HSA as a plasma volume expander.

VII. Thiolation of HexaPEGylated Albumin

Thiocarbamoyl human serum albumin exhibits molecular properties comparable to that of hexaPEGylated human serum albumin generated by extension arm facilitated PEGylation, and is a good plasma expander just as the hexaPEGylated albumin that was generated by the extension arm facilitated maleimide chemistry based PEGylation. Accordingly, additional molecular properties can be introduced to PEGylated albumin to increase its clinical applications.

Figure 10:
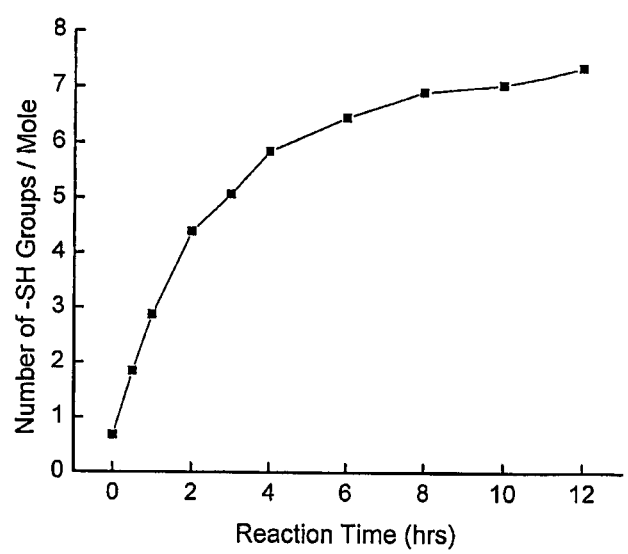
FIG. 10. Kinetics of thiolation of (Thiocarbamoyl Phenyl PEG-5K) human serum albumin.

One such contemplated molecular property is to facilitate the transport of nitric oxide (NO) when the PEGylated albumin is in the plasma, i.e. to facilitate the transport of NO by PEGylated albumin by generating PEGylated and thiolated human serum albumin, where the thiol groups can transport NO as S-nitroso derivatives. Transport of NO by the protein thiols is an established mechanism for the transport of the oxygen. Reaction of iminothiolane with thiocarbomoyl PEG albumin generated the desired PEGylated thiolated human serum albumin. FIG. 10 presents the kinetics of thiolation of the PEGylated protein with iminothiolane at a protein concentration of 0.5 mM and an iminothiolane concentration of 10 mM at pH 7.4 and 4° C. Stopping the reaction at a given time point generates the PEGylated product with the desired level of thiol groups. By increasing the concentration of iminothiolane to 40 mM, as many as nearly 20 thiol groups could be introduced per molecule.

Another molecular property that has been engineered into the PEGylated albumin is an added ability for the PEGylated molecule to scavenge free radicals in the circulatory system. Increased levels of free radicals is the consequence of oxidative stress in biological systems. Polynitroxylation of proteins is an approach that has been advanced to facilitate the scavenging of such free radicals. Covalent attachment of nitroxyl radicals is engineered onto PEGylated protein by the thiolation mediated maleimide chemistry based approach; a polynitroxylated PEGylated albumin has been prepared by reacting PEGylated albumin with maleimide proxyl (or maleimide tempol) in the presence of iminothiolane. In the present study, PEGylated polynitroxylated albumin has been now generated. Thus, these PEGylated albumin molecules can achieve both vasodilation and scavenging of free radical when in the circulation.

VIII. Thiolation Mediated Non-Conservative PEGylation of Proteins

Figure 11:
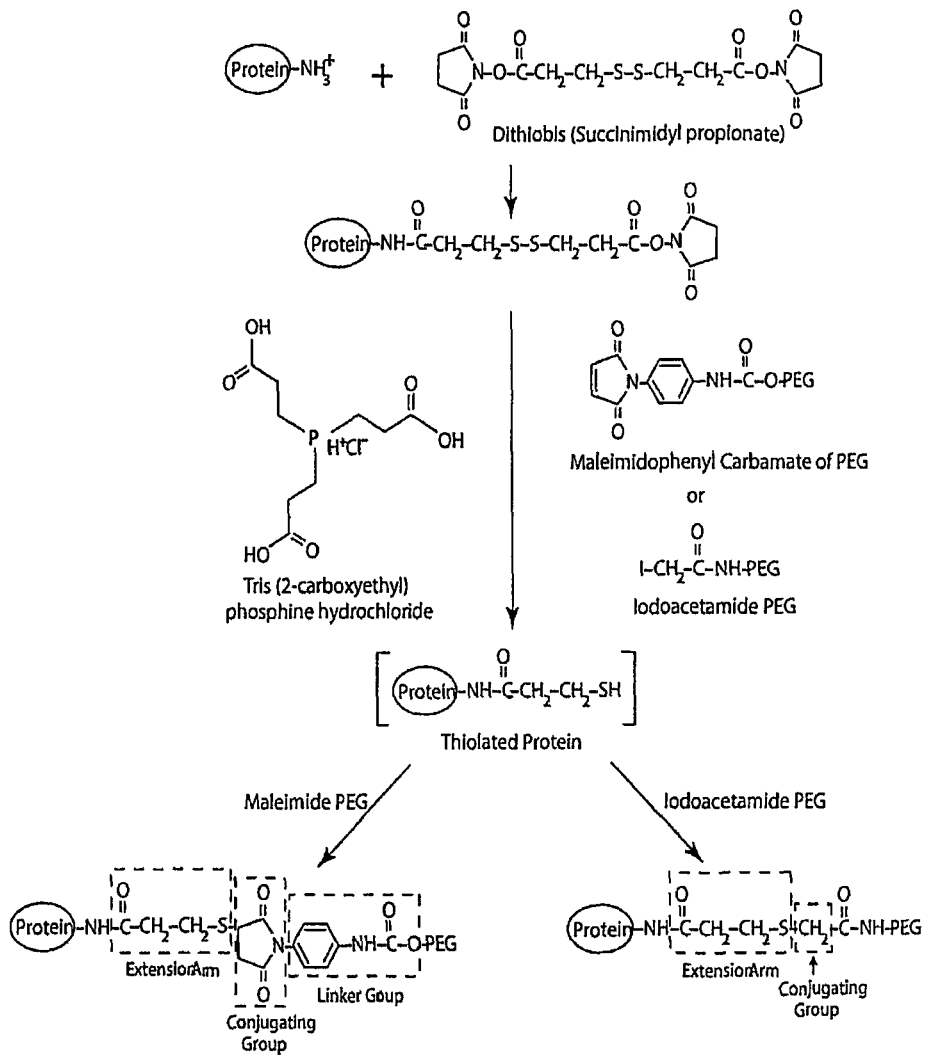
FIG. 11. Schematic representation of thiolation mediated non-conservative PEGylation of Proteins. The thiol groups are generated on the protein by reaction with bis succinimidyl dithiopropionimidate followed by reduction of the disulfide bonds with tris carboxyethyl phosphine and then subjected to PEGylation either using maleimide PEG or iodoacetamido PEG just as in the thiolation mediated conservative PEGylation.

The ε-amino groups of the Lys residues of proteins can also be thiolated using bis succinimidyl dithio propionate (DTSP) or dithio sulfosuccinimidyl propionate (DTSSP) (FIG. 11). In this protocol, the protein is thiolated at the ε-amino groups by the acylation chemistry and accordingly the thiolation of the protein is accompanied by a loss of the positive charge of the ε-amino groups derivatized. The protein is first derivatized with the bifunctional disulfide bridged active ester under conditions wherein, predominantly, a monofunctional modification of the protein is accomplished. The excess reagent is separated from the modified protein, and the modified protein is converted to a thiolated protein in the presence of maleimide using non-thiol reducing agents, for example, tris carboxyethyl phosphine. This thiolation mediated PEGylation protocol has been developed to generate a new class of PEGylated proteins.

Since the solution properties of the PEGylated protein are not a direct consequence of PEG mass, the charge of the amino group influences the consequence of PEGylation. Accordingly, one can choose the PEGylation strategy to manipulate (customize) the solution properties of PEG-Hb and PEG albumin.

Instead of using dithiosuccinimidyl propionate (acylation chemistry), one could use dithiobispropionimidate (amidation chemistry) to achieve the thiolation without altering the positive charge at the site of the attachment of the extension arm.

The flexibility of the thiolation mediated PEGylation protocol can be increased by using other functionalized PEG regents specific for sulhydryl groups, e.g. iodoalkylamide PEG derivatives, vinyl sulfone PEGs and mixed disulfides of PEG.

Besides PEGylated albumin generated by thiolation mediated PEGylation, PEG-albumin has also been generated using isothiocyanato chemistry based PEGylation.

Both the conservative and non-conservative thiolation protocols discussed in this disclosure engineer an "extension arm" between the protein and the PEG-chain as compared to the simple nonconservative PEGylation that involves the formation of an isopeptide bond (PEG conjugating group) directly on the ε-amino group of the protein. The "extension arm" introduced between the PEG and protein appears to reduce the propensity of the PEG chain to endow the PEGylated protein with a higher viscosity and colloidal osmotic pressure.

The engineering of the extension arm also increases the accessibility of the newly introduced thiol groups. The flexibility of the thiolation protocol can be increased to manipulate the solution properties of PEGylated protein and/or accessibility of the new thiol groups by varying the length of the extension arm from 3 to 4, six to eight carbon atoms by using propioic acid, butyric acid, caproic acid or caprylic acid as the extension arm, using either acylation or amidation chemistry to attach the extension arm that has a thiol group at the distal end protected either as a symmetrical disulfide of a mixed disulfide. Dithiopyridyl group is used to generate a mixed disulfide that can be used for protein thiolation.

The general structure of the reagent that can be used for the engineering of the 'extension arm' is a thiopyridyl succinimidyl (sulfosuccinimidyl) derivative or thiopyridyl imidate ester of omega mercapto derivative of an aliphatic carboxylic acid, and is represented by a general structure

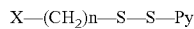

$$X-(CH_2)n-S-S-Py$$

wherein X could be a succinimidyl carboxylate or sulfosuccinimidyl carboxylate or an imidate, n=2, proponic acid derivative, n=2, butyric acid derivative, n=5, caproic acid derivative, n=7, caprylic acid, or any other omega mercapto aliphatic acid depending the desired length of the extension arm. When acylation chemistry is used for linking the extension arm to the protein, as the length of the alkyl chain of the extension arm increases, it may be useful to employ sulfosuccinimdyl derivative as the sulfo derivative is likely to be more soluble than the succinimidyl derivative. The amidation chemistry will attach the extension arm to the surface amino group without altering the net charge of the protein (conservative modification); the acylation chemistry mediated linking of the extension arm alters the net surface charge of the protein (non-conservative modification).

IX. Discussion

PEGylation, the conjugation of PEG-chains to proteins, has become a very useful approach in biotechnology in the development of peptide and protein therapeutics. The conjugation of a given PEG mass to a peptide/protein could be achieved by either conjugating multiple copies of small PEG-chains or a limited number of larger PEG-chains. The preferred pattern of PEGylation appears to be dictated by the function that the PEGylated protein is expected to perform in vivo.

Thiolation mediated maleimide chemistry based PEGylation increases the accessibility of the surface amino groups of proteins for PEGylation through the step of thiolation by engineering 'extension arms' on the reactive surface amino groups of proteins. The thiolation step also makes it possible to use the very selective maleimide chemistry for PEGylation of proteins. On reaction of the protein with 2-iminothiolane (δ-mercapto butyrimidation), new thiol groups are introduced at the reactive ε-amino groups at a distance of four carbon atoms (approximately 9 to 10 Angstroms) away from the original nitrogen atom of the amino group. The new thiol groups are used as the target sites for the very selective maleimide chemistry based conjugation with PEG.

Albumin and Hb have been now subjected to PEGylation using a modified thiolation mediated PEGylation protocol that involves the capping step using N-ethyl maleimide at the end of the PEGylation reaction. Properties of the PEGylated albumin and PEGylated Hb generated by the modified thiolation mediated protein PEGylation platform have been described, along with the potential therapeutic application of PEGylated albumins as a plasma volume expander and that of PEGylated Hbs as an oxygen carrying plasma volume expander.

The thiolation of proteins based on the amidination of the reactive ε-amino groups and subsequent PEGylation does not neutralize the original positive charge of the ε-amino groups; accordingly this approach is referred to as conservative PEGylation. The iminothiolane mediated thiolation of proteins has been coupled with alkylation chemistry to develop a thiolation mediated alkylation chemistry based PEGylation as an alternate conservative PEGylation protocol.

A non-conservative thiolation protocol based on acylation chemistry has also been developed. In this case the thiol groups are introduced on the reactive surface amino groups by acylation using a disulfide based bifunctional reagent and subsequent reduction of the disulfide bond to expose free thiol groups on the proteins. These thiols can then be PEGylated using either PEG maleimide or iodoactamide PEG. The acylation chemistry based thiolation of the amino groups is accompanied by the loss of the positive charge of the amino group. Therefore, acylation chemistry based thiolation of protein followed by PEGylation is referred to as nonconservative thiolation mediated PEGylation. The same principle could be used using bis dithiopropinimidate, wherein the thiolation can be achieved by the amidation chemistry just as the iminothiolation mediated PEGylation, which will be again conservative thiolation mediated PEGylation. The thiolation mediated (i) succinimidylation chemistry based and (ii) alkylation chemistry based PEGylation strategies in the conservative as well as nonconservative modes are expected to facilitate the design of new plasma volume expanders and oxygen carrying plasma volume expanders.

The general principles of the thiolation based PEGylation will also facilitate the conjugation of multiple copies of other sulfhydryl group specific reagents as well as PEG reagents, mixed disulfides of thiol PEG, and PEG vinyl sulfone to proteins. Similarly, dextran and hydroxyethyl starch plasma volume expanders could also be coupled to proteins using the thiolation based platform by derivatizing these into sulfhydryl group specific reagents. The hybrid albumin/Hb products with unique properties could be produced for special clinical applications.

PEGylation of Hb has turned out to be an alternate approach to overcome the vasoactivity of acellular Hb, and this is achieved by making the solution of Hb a plasma volume expander. The efficiency of albumin, which itself has been used as a plasma volume expander, is significantly enhanced on PEGylation, and PEGylation of albumin also induces some new clinical properties to Hb. During the course of comparison of the molecular properties of PEGylated albumin and PEGylated Hb, it was seen that efficiency of increasing colloidal osmotic pressure is better with Hb than with albumin, even though both proteins have similar molecular mass. This prompted an investigation of the influence of the presence of an intramolecular crossbridge into Hb on the PEGylation induced molecular properties and structural features of Hb.

The three PEGylation induced molecular properties of Hb that have considered as the players in the neutralization of the vasoactivity of Hb are (i) enhanced molecular volume (hydrodynamic volume), (ii) viscosity and (iii) colloidal osmotic pressure. The increase in the molecular volume of Hb resulting from PEGylation has been quantitated by three different approaches: (i) by calculation of the molecular radius based on the colloidal osmotic pressure, (ii) by size exclusion chromatography of the PEGylated Hb on superose-12 columns and (iii) by determination of molecular radius by dynamic light scattering. The molecular radius of Enzon PEGylated Hb was calculated by Vandegriff and her colleagues based on the colloidal osmotic pressure of PEGylated bovine Hb, and a value of 15 nm was assigned to this decaPEGylated bovine Hb. The non-hypertensive PEGylated Hb generated by extension arm facilitated PEGylation [(SP-PEG-5K)$_6$-Hb] (Acharya et al., 2005) was estimated to be around 14 nm when calculated based on the colloidal osmotic pressure. However, the value of this hexaPEGylated Hb as determined by dynamic light scattering is around 6 nm (Manjula et al., 2005). The hexaPEGylated Hb generated by reductive alkylation chemistry is around 5.5 nm as determined by dynamic light scattering. Consistent with this the hydrodynamic volume of two hexaPEGylated Hb generated by using two different chemistries is nearly the same as reflected by size exclusion chromatography (Hu et al., 2005). This hydrodynamic volume of hexaPEGylated product is comparable to that of the oligomer of Hb that carries four copies of the tetramer, which is generated by the intermolecular crosslinking of Hb.

Given the fact that the colloidal osmotic pressure of (Propyl-PEG-5K)$_6$-Hb is nearly the double that of (SP-PEG-5K)$_6$-Hb (Hu et al., 2005), the molecular radius of this hexaPEGylated Hb if calculated based on its COP will be even higher than that of decaPEGylated bovine Hb of Enzon. This is thought to reflect the influence of chemistry of PEGylation (conjugation) on the PEGylation induced colloidal osmotic pressure of the protein. The hexaPEGylated Hb generated by acylation chemistry that neutralizes the positive charge of the surface amino groups of Hb was even higher than that of (Propyl-PEG5K)$_6$-Hb. Thus, there appears that there is no correlation between the PEGylation induced size enhancement (molecular radius) and COP.

The present study revealed that the intramolecular crossbridge has a significant influence on the PEGylation induced increase in the molecular volume and decrease in the colloidal osmotic pressure. The molecular volume increase on hexaPEGylation of Hb is nearly doubled by the presence of intramolecular crosslinking. On the other hand, the COP is lowered at least by 30 to 35% by the presence of intramolecular crosslinks. These two influences are independent of the chemistry and the location of intramolecular crosslinks. Both inside the central cavity, very short and rigid crossbridges, as well as outside the central cavity, flexible and long crossbridges, exhibited nearly identical responses, suggesting that the prevention of the dissociation of the PEGylated Hb into dimers is the primary molecular aspect for the modulation of the PEGylation induced molecular properties of Hb.

Confirmation of the influence of intra molecular crossbridges in increasing molecular size of PEGylated Hb comes from the analytical ultracentrifugation studies. An increase in the molecular size reflects the prevention of the dissociation of the PEGylated tetramer. A comparison of the S-values of the PEGylated Hb and PEGylated αα-fumaryl crossbridged Hb clearly showed that the two molecules are very distinct in terms of the S-values, with the crossbridged molecule exhibiting a higher S-value. The M$_w$ value of the PEGylated crossbridged molecule is ~90 K, while that of the PEGylated uncrosslinked Hb is around ~60 K, reflecting the smaller molecular mass of the PEGylated uncrosslinked material. The concentration dependence of S values, confirms that hexaPEGylation of uncrosslinked Hb increases the dissociation of the tetramer into dimers. It should also be noted that the S values of the PEGylated molecules are lower than the corresponding parent molecules, even though a mass of nearly ~30 K has been conjugated to the tetramer. Thus PEGylation of Hb increases the resistance of the molecule to sediment, and this may be an important aspect of the molecule in terms of the biological significance of Hb. In this respect, the behavior of the PEGylated Hbs may be compared to that of lipoproteins that are characterized by their floatation patterns.

Thus, the consequence of PEGylation, particularly in terms of the molecular properties that could be endowed to the molecule is influenced by the presence of intramolecular crossbridges. The significantly enhanced molecular volume and the lower colloidal osmotic pressure of (Propyl-PEG5K)$_6$-αα-Hb relative to the (Propyl-PEG5K)$_6$-Hb makes the crosslinked Hb a better substrate than uncrosslinked Hb for blood substitutes. The higher molecular volume of the PEGylated crosslinked Hb will further reduce the slow, but nonetheless possible, extravasation of PEGylated uncrosslinked Hb. In addition, the lower COP of the PEGylated crosslinked Hb relative to that of PEGylated uncrosslinked Hb makes it possible to use a higher concentration of Hb, without the possible dilution of the infused Hb by an increase in flow of fluids from the interstitial tissues to the vascular system. This has been the major limitation of the current versions of PEGylated Hbs in attempts to increase the level of tissue oxygenation. The absence of significant influence of intramolecular crosslinks on the viscosity of PEGylated Hb suggests that the viscosity of PEGylated Hb is a direct correlate of the PEG conjugated to protein (protein to PEG ratio). However, it should be noted that the viscosity as well as COP of a mixture of methoxy-PEG (amount being comparable to that of hexaPEGylated Hb) and Hb is very low as compared to that of PEGylated Hb. This reflects the need for the covalent attachment of PEG-chains to Hb to induce the molecular properties discussed here. This may reflect the fact that on conjugation, the PEG is defined in a defined domain surrounding the protein core (PEG-shell), and it will be hard if not impossible to achieve such a high concentration of PEG in the solution to mimic that effect.

A very interesting result of the present study is that the rate of sedimentation of Hb is reduced on conjugation of PEG-chains to the protein, even though the molecular mass of the PEG-Hb conjugate is higher than that of the unmodified sample. This is apparently the contribution of the PEG-shell around the protein core which lowers the rate of sedimentation of the conjugate. This propensity of the conjugated PEG to reduce the rate of sedimentation of the protein is independent of the presence of intramolecular crosslinks. The major consequence of conjugation of multiple copies of PEG-5K chains to Hb is an unusual enhancement in the molecular volume of the protein to the given the mass of PEG-chain conjugated. This results in a very low density of atoms in the PEG-shell relative to that in the protein core. During sedimentation analysis, reorientation of the low density PEG shell causes the covalently attached PEG-chains to behave as a parachute, increasing the hydrodynamic drag on the molecule and slowing down the rate of sedimentation. It is conceivable that similar influence is exerted by the PEG-chains when the PEG-Hb is used as blood substitute and introduced into the circulatory system. In this situation the interaction of the reoriented PEG-chains with the endothelium at the blood tissue interface may provide an additional mechanical stimulus that is different from that due to shear stress developed on the endothelial surface determined by the local shear rate and the bulk viscosity of the medium. The potential role of PEGylated proteins in providing additional mechanism of interaction with the endothelium has important physiological/biological consequences because it would allow lowering overall viscosity while maintaining the necessary level of mechanical stimulation of the endothelium, necessary for mechano transduction mediated homeostasis. A direct practical consequence of theses findings is the development of these PEGylated proteins as new and effective plasma volume expanders.

A major finding of the present work is that PEGylated uncrosslinked Hb generated by reductive alkylation chemistry predominantly exits as dimers as reflected by size exclusion chromatography. A comparison of the SEC of the crosslinked and uncrosslinked PEGylated products at two concentrations (5 µM and 1 µM) showed that the same difference exits in the hydrodynamic volume of two PEGylated proteins at both protein concentrations tested. Nonetheless it should be noted that during SEC, there is a degree of dilution of the sample, which may contribute to the shift in the equilibrium between the tetramer and the dimers as compared to that in the bulk solution. However, the predominant presence of dimeric forms of (Propyl-PEG5K)$_6$-Hb in 4 gms % solution of the product is reflected by the COP data.

The influence of the crosslinks in the PEGylated Hb is also reflected in the circular dichroic spectra and fluorescence spectra of the products. The CD measurements reflect the perturbation of the heme environment and the fluorescence data suggest perturbation of the $\alpha_1\beta_2$ interface of Hb by PEGylation, and a reduced effect of PEGylation on these structural aspects by the presence of $\alpha\alpha$L-fumaryl crossbridge. Thus, even from the structural point of view, the intramolecular crosslinked Hbs appear to be a better substrate for PEGylation to generate PEGylated Hb as blood substitutes.

The molecular basis for enhancing the dissociation of Hb tetramers into dimers upon PEGylation is also of interest from a structural point of view. Typically, association of dimers into tetramers is driven primarily by formation of the $\alpha1\beta2$ interface that involves more polar contacts between the C and N termini and the C-helices and FG corners of both subunits. Since the complete modification of N-termini has taken place in the reductive alkylation chemistry, this can influence the interactions at both the $\alpha\alpha$ and the $\beta\beta$-ends of the central cavity. In addition, the association of $\alpha\beta$ dimers to tetramers is facilitated by electrostatic attraction between positively charged $\alpha$ subunits and negatively charged $\beta$ subunits. The new hydrated PEG-shell around the protein core generated by the covalently attached PEG chain to Hb molecule can also shield the charge of $\alpha$ and $\beta$ subunits, which in turn can decrease the intersubunit electrostatic attractions either through perturbation of the hydration within the central cavity or a direct consequence of the perturbation of the hydration shell of Hb by the presence of the new hydrated PEG-shell.

REFERENCES

Abuchowski, A., Es, T. V., Palczuk, N. C. and Davis, F. F. (1997a) Alteration of immunological properties of bovine serum albumin by covalent attachment of polyethylene glycol. J. Biol. Chem. 252:3578-3581.

Abuchowski, A., McCoy, J. R., Palczuk, N. C., Es, T. V. and Davis, F. F. (1997b) Effect of covalent attachment of polyethylene glycol on immunogenicity and circulating life of bovine liver catalase. J. Biol. Chem. 252:3582-3586.

Acharya, A. S., Manjula, B. N, and Smith, P. K. Hemoglobin Crosslinkers. (1996) U.S. Pat. No. 5,585,484.

Acharya A. S., Intaglietta M., Tsai A. G., Malavalli A, Vandegriff K., Winslow R. M., Smith P. K., Friedman J. M., and Manjula B. N. (2003) (PEG5K)$_6$-Hb: A non-hypertensive hemoglobin molecule generated by conservative PEGylation. Abstract, The 9$^{th}$ International Symposium on Blood Substitutes, Tokyo, Japan, March 2003.

Acharya, A. S., Intaglietta, M., Tsai, A. G., Malavalli, A., Vandegriff, K., Winslow, R. M., Smith, P. K., Friedman, J. M., and Manjula, B. N. (2005) Enhanced molecular volume of conservatively PEGylated Hb: (SP-PEG5K)$_6$-HbA is non-hypertensive. Artificial cells, Blood Subs. Biotechnol. 33: 239-255.

Alayash, A I, Summers A G, Wood F, Jia Y. (2001) Effects of glutaraldehyde polymerization on oxygen transport and redox properties of bovine hemoglobin. Arch. Biochem. Biophys. 391: 225-234.

Bailon, P., and Berthold, W. (1998) Polyethylene glycol-conjugated pharmaceutical proteins Pharm. Sci. Technol. Today 1: 352-356.

Chang T M S. (1999) Future prospects for artificial blood. Trends Biotechnol. 17: 61-67.

Chatterjee R, Welty E V, Walder R Y, Pruitt S L, Rogers P L, Arnone A, Walder J A. (1986) Isolation and characterization of a new hemoglobin derivative cross-linked between the $\alpha$ chains (lysine 99$\alpha$1-lysine 99$\alpha$2). J. Biol. Chem. 261: 9929-9937.

Cheng, Y., Shen T., Simplaceanu, V. and Ho, C. (2002) Ligand binding properties and structural studies of recombinant and chemically modified hemoglobins altered at beta 93 cysteine. Biochemistry. 41: 11901-11913.

Dhalluin C, Ross A, Leuthold L A, Foser S, Gsell B, Muller F, Senn H. (2005) Structural and biophysical characterization of the 40 kDa PEG-interferon-alpha2a and its individual positional isomers. Bioconjug Chem. 16: 504-517.

Doyle, M. P., Apostol, I., and Kerwin B. A. (1999) Glutaraldehyde modification of recombinant human hemoglobin alters its hemodynamic properties. J. Biol. Chem. 274: 2583-2591.

Gulati A, Barve A, Sen A P. (1999) Pharmacology of hemoglobin therapeutics. J. Lab. Clin. Med. 133: 112-119.

Harris, J. M., and Chess, R. B. (2003) Effect of PEGylation on pharmaceuticals. Nat. Rev. Drug Discov. 2: 214-221.

Harris, J. M., and Zalipsky, S. (1997) Poly(ethylene glycol) chemistry and biological applications. Am. Chem. Soc. Symposium Series 680: 1-15.

Hirsch, R. E. (2003) Hemoglobin fluorescence. Methods Mol. Med. 82: 133-154.

Hsu, M. C., and Woody, R. W. (1971) The origin of the heme Cotton effects in myoglobin and hemoglobin. J. Am. Chem. Soc. 93: 3515-3525.

Hu, T., Prabhakaran, M., Acharya, S. A., Manjula, B. N. (2005) Influence of the chemistry of conjugation of poly (ethylene glycol) to Hb on the oxygen-binding and solution properties of the PEG-Hb conjugate. Biochem. J. 392: 555-564.

Iwasaki, K. and Iwashita, Y. (1987) Hemoglobin combined with poly(alkylene oxide). U.S. Pat. No. 4,670,417.

Juszczak, L. J., Manjula B. N., C. Bonaventura, Acharya A. S., and Friedman J. M. (2002) UV Resonance Raman study of −93-modified hemoglobin A: Chemical modifier-specific effects and added influences of attached poly(ethylene glycol) chains. Biochemistry 41: 376-385.

Kellett, G. L. (1971) Dissociation of hemoglobin into subunits: ligand-linked dissociation at neutral pH. J. Mol. Biol. 59: 401-424.

Khan, I, D. Dansker, U. Samuni, A. J. Friedman, C. Bonaventura, Manjula B. N., Acharya A. S., and Friedman J. M. (2001) Cys-93( ) modified hemoglobin: Kinetic and conformational consequences. Biochemistry 40: 7581-7592.

Klein, H G. (2000) The prospects for red-cell substitutes. New Engl. J. Med. 342: 1666-1668.

Kramer G C. (2003) Counterintuitive red blood cell substitute—Polyethylene glycol-modified human hemoglobin. Crit. Care. Med. 31:1882-1883.

Lippincott, J., Hess, E., and Apostol, I. (1997) Mapping of recombinant hemoglobin using immobilized trypsin cartridges. Anal. Biochem. 252: 314-325.

Manjula, B. N., and Acharya, A. S. (2003) In 'Methods in Molecular Medicine: Hemoglobin Disorders: Molecular Methods and Protocols', Ed. Nagel R. L. 82, pp 31-47. Humana Press, Totowa, N.J.

Manjula, B N, Malavalli, A, Smith, P K, Chan, N L, Arnone, A, Friedman, J M, Acharya A S (2000) Cys-93-ββ-succinimidophenyl polyethylene glycol 2000 hemoglobin A. J. Biol. Chem. 275: 5527-5534.

Manjula, B. N., Tsai, A. G., Intaglietta, M., Tsai, C-H., Ho, C., Smith, P. K., Perumalsamy, K., Kanika, N. D., Friedman, J. M., and Acharya, A. S. (2005) Conjugation of multiple copies of polyethylene glycol to hemoglobin facilitated through thiolation: Influence on hemoglobin structure and function. Protein J. 42: 133-146.

Manjula B. N., Tsai A., Upadhya R., Perumalsamy K., Smith P. K., Malavalli A, Vandegriff K. D., Winslow R. M., Intaglietta M., Prabhakaran M., Friedman J. M., and Acharya A. S. (2003) Site-specific PEGylation of hemoglobin at Cys-93(β): Correlation between the colligative properties of the PEGylated protein and the length of the conjugated PEG chain. Bioconjugate Chem. 14: 464-472.

Manjula B. N., Upadhya R., Nemkal, A., Smith P. K., Vandegriff K. D., Winslow R. M., Friedman J. M., and Acharya A. S. (2000) Site-specific surface decoration of hemoglobin-A with polyethylene glycol: Correlation between increased hydrodynamic volume and mass of PEG conjugated. *Abstract, VIII International Symposium on Blood Substitutes, San Diego, Calif.* November 2000.

Perutz, M. F., Ladner, J. E., Simon, S. R., and Ho. C. (1974) Influence of globin structure on the state of the heme. I. Human deoxyhemoglobin. Biochemistry 13: 2163-2173.

Rao, M. J., Schneider, K., Chait, B. C., Chao, T. L., Keller, H. L., Anderson, S. M., Manjula, B. N., Kumar, R. A., and Acharya, A. S. (1994) Recombinant hemoglobin A produced in transgenic swine: structural equivalence with human hemoglobin A. Artificial Cells, Blood Substitutes and Immobilization Biotechnology 22: 695-700.

Rohlfs, R. J., E. Bruner, A. Chiu, A. Gonzales, M. L. Gonzales, M. D. Magde, K. D. Vandegriff, and R. M. Winslow. (1998) Arterial blood pressure responses to cell-free hemoglobin solutions and the reaction with nitric oxide. *J. Biol. Chem.* 273:12128.

Tsai, A. G. and Intaglietta, M. (2002) The unusual properties of effective blood substitutes. *Keio J. Med.* 51: 17-20.

Vandegriff, K. D., McCarthy, M., Rohlfs, R. J. and Winslow R. M. (1997a) Colloid osmotic properties of modified hemoglobins: chemically cross-linked versus polyethylene glycol surface-conjugated. *Biophysical Chemistry* 69: 23-30.

Vandegriff, K. D., Rohlfs, R. J. and Winslow R M. (1997b) Colloid osmotic effects of hemoglobin-based oxygen carriers. *Advances in Blood Substitutes. Industrial Opportunities and Medical Challenges.* Winslow, R. M., Vandegriff, K. D. and Intaglietta, M. eds. Pp 207-227, Birkhauser, Boston.

Vandegriff K. D., Malavalli A, Wooldridge J., Lohman J., and Winslow R. M. (2003) MP4, a new nonvasoactive PEG-Hb conjugate. *Transfusion* 43: 509-516.

Winslow, R. M. (2000) αα-crosslinked hemoglobin: was failure predicted by preclinical testing? Vox. Sang. 79: 1-20.

Zentz, C., Pin, S., and Alpert, B. (1994) Stationary and time-resolved circular dichroism of hemoglobins. Methods Enzymol. 232, 247-266.

What is claimed is:

1. A method of expanding the volume of plasma in a subject in need thereof comprising administering to the subject a plasma volume expander in an amount effective to expand plasma volume, wherein the plasma volume expander comprises a PEGylated albumin having a colloid osmotic pressure of 37-40 mm Hg and a viscosity of 2.0 to 4.0 cP, wherein the PEGylated albumin comprises 6-18 maleimide phenyl polyethylene glycol (PEG) chains, wherein each PEG chain has a molecular weight of 3,000-20,000 daltons, and wherein each maleimide phenyl polyethylene glycol (PEG) chain is conjugated to a thiolated amino group of albumin.

2. The method of claim 1, wherein the thiolated amino group of albumin is generated using dithio sulfo succinimidyl propionate (DTSSP) or dithiosuccinimidyl propionate (DTSP) or dithiobispropionimidate or iminothiolane or a reagent having a structure X—$(CH_2)_n$—S—S—Py, wherein X is a succinimidyl carboxylate or a sulfosuccinimidyl carboxylate or an imidate, n=2-7, and Py represents pyridine moiety.

3. The method of claim 1, wherein each PEG chain of the PEGylated albumin has a molecular weight of 3,000 to 5,000 daltons.

4. The method of claim 1, wherein each PEG chain of the PEGylated albumin has a molecular weight of 5,000 daltons.

5. The method of claim 1, wherein 12 PEG chains are conjugated to albumin.

6. The method of claim 1, wherein the PEGylated albumin has a viscosity of 2 to 3.7 cP.

7. The method of claim 1, wherein the plasma volume expander comprises nitroxyl radicals covalently attached to the thiolated PEGylated albumin.

* * * * *